US009080986B2

(12) United States Patent
Hirai et al.

(10) Patent No.: US 9,080,986 B2
(45) Date of Patent: Jul. 14, 2015

(54) TRANSPARENT OBJECT DETECTION SYSTEM AND TRANSPARENT FLAT PLATE DETECTION SYSTEM

(75) Inventors: Hideaki Hirai, Kanagawa (JP); Shin Aoki, Kanagawa (JP); Masanori Kobayashi, Kanagawa (JP); Xue Li, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 367 days.

(21) Appl. No.: 13/520,858

(22) PCT Filed: Jan. 26, 2011

(86) PCT No.: PCT/JP2011/052073
§ 371 (c)(1),
(2), (4) Date: Jul. 6, 2012

(87) PCT Pub. No.: WO2011/099404
PCT Pub. Date: Aug. 18, 2011

(65) Prior Publication Data
US 2013/0123985 A1 May 16, 2013

(30) Foreign Application Priority Data

Feb. 15, 2010 (JP) ................................. 2010-030238
Feb. 15, 2010 (JP) ................................. 2010-030247

(51) Int. Cl.
*G06K 9/00* (2006.01)
*G01N 21/84* (2006.01)
(Continued)

(52) U.S. Cl.
CPC .............. *G01N 21/84* (2013.01); *B25J 9/1697* (2013.01); *G01N 21/21* (2013.01); *G01N 21/958* (2013.01); *G01N 21/23* (2013.01); *G01N 21/9018* (2013.01); *G01N 21/9027* (2013.01)

(58) Field of Classification Search
CPC ....................................................... B25J 9/1612
USPC ............................................................ 382/141
See application file for complete search history.

(56) References Cited

U.S. PATENT DOCUMENTS 5,557,324 A * 9/1996 Wolff ............................. 345/207
5,841,538 A * 11/1998 Schoeffler et al. ............ 356/369
(Continued)

FOREIGN PATENT DOCUMENTS

| CN | 1908638 A | 2/2007 |
| JP | 63 132143 | 6/1988 |

(Continued)

OTHER PUBLICATIONS

Office Action issued Sep. 10, 2013, in Japanese Patent Application No. 2010-030247.
(Continued)

*Primary Examiner* — Gregory M Desire
(74) *Attorney, Agent, or Firm* — Oblon, McClelland, Maier & Neustadt, L.L.P.

(57) ABSTRACT

A disclosed transparent body detection system includes an image acquisition unit acquiring a vertical polarization image and a horizontal polarization image by acquiring an image of a first region, the image including a transparent body having characteristics in which a polarization direction of transmission light changes; a placing table on which the transparent body is to be placed; a polarization filter disposed opposite to the image acquisition unit across the placing table and at a position including a second region, an image of the second region including at least the transparent body in the first region and being acquired; and an image processing apparatus detecting the transparent body based on distribution of vertical/lateral polarization degree of a vertical/lateral polarization degree image based on the vertical polarization image and the horizontal polarization image.

17 Claims, 23 Drawing Sheets

(51) Int. Cl.
*G01N 21/21* (2006.01)
*G01N 21/958* (2006.01)
*B25J 9/16* (2006.01)
*G01N 21/23* (2006.01)
*G01N 21/90* (2006.01)

(56) References Cited

U.S. PATENT DOCUMENTS

| | | | |
|---|---|---|---|
| 7,347,817 B2 * | 3/2008 | Glukhovsky et al. | 600/181 |
| 7,352,889 B2 * | 4/2008 | Ganz et al. | 382/141 |
| 7,406,189 B2 * | 7/2008 | Ganz et al. | 382/133 |
| 2003/0099382 A1 * | 5/2003 | Ganz et al. | 382/128 |
| 2004/0129901 A1 * | 7/2004 | Yamaguchi et al. | 250/559.07 |
| 2005/0078306 A1 | 4/2005 | Engels | |
| 2007/0239315 A1 * | 10/2007 | Sato et al. | 700/245 |
| 2010/0208060 A1 * | 8/2010 | Kobayashi et al. | 348/135 |

FOREIGN PATENT DOCUMENTS

| | | |
|---|---|---|
| JP | 4 282440 | 10/1992 |
| JP | 5 18889 | 1/1993 |
| JP | 9 166552 | 6/1997 |
| JP | 2001 141670 | 5/2001 |
| JP | 2002 98650 | 4/2002 |
| JP | 2005 120563 | 5/2005 |
| JP | 2007-57244 A | 3/2007 |
| JP | 2008-45959 A | 2/2008 |

OTHER PUBLICATIONS

Combined Chinese Office Action and Search Report issued Jan. 30, 2014 in Patent Application No. 201180009141.4 (with English translation).

Office Action issued Nov. 29, 2013, in Korean Patent Application No. 10-2012-7021110 with English translation.

International Search Report Issued Mar. 29, 2011 in PCT/JP11/52073 Filed Jan. 26, 2011.

* cited by examiner

FIG.20A
FIG.20B
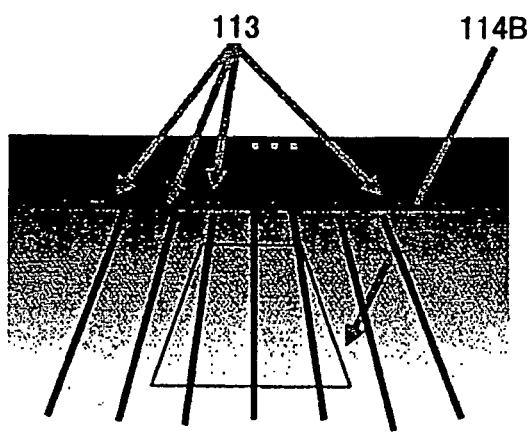
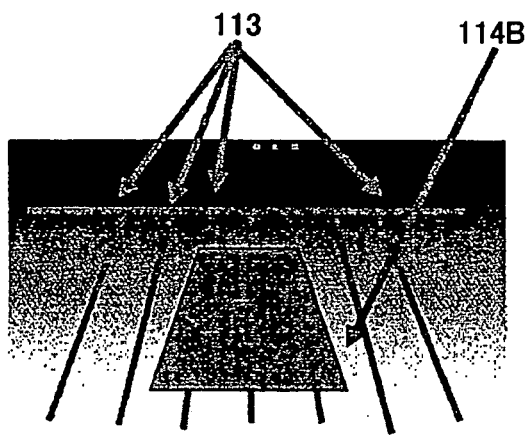

FIG.30A
FIG.30B
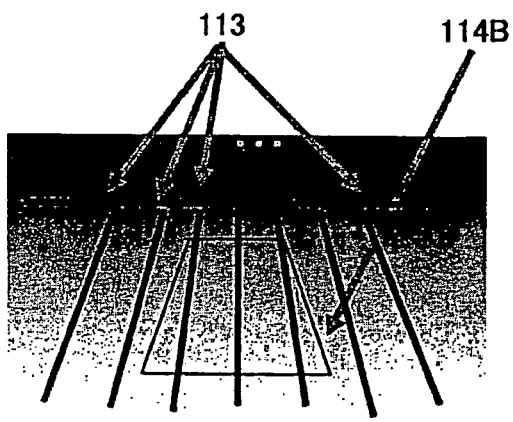
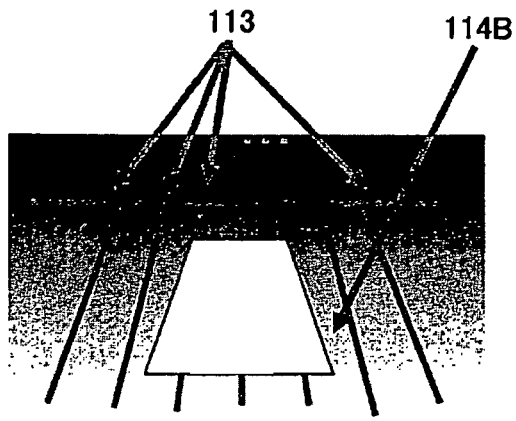

TRANSPARENT OBJECT DETECTION SYSTEM AND TRANSPARENT FLAT PLATE DETECTION SYSTEM

TECHNICAL FIELD

The present invention relates to a transparent object detection system and a transparent flat plate detection system, and particularly to a transparent object detection system and a transparent flat plate detection system easily and accurately detecting a transparent object and a transparent flat plate, respectively, based on image processing.

BACKGROUND ART

Conventionally, transparent plastic molded objects (hereinafter "transparent object(s)") are used in various fields such as food wrappers, household electrical appliances, vehicle parts and the like and also widely used as optical parts such as displays, optical disks and the like. However, when such a transparent object is treated as an object to be imaged, it may be difficult to properly detect the transparent object with a typical camera that can detect only luminance information. This is because the transparent object has a low reflection rate and high transmissivity. Therefore, an obtained contrast between the transparent object and the background is likely to become unclear.

To resolve the problem, Patent Document 1 discloses a transparent object detection method to be used in a transparent body detection system of FIG. 1. As schematically illustrated in FIG. 1, the transparent body detection system includes a light projecting side polarization plate 95, a light projecting device 91, a polarization apparatus 92 having a light receiving side polarization plate 96, a TV camera 93, and an image processing apparatus 94. The light projecting side polarization plate 95 polarizes light in a specific direction. The light projecting device 91 projects light to a predetermined region including a transparent object 90. The light receiving side polarization plate 96 transmits only specific polarized light from the light having transmitted through the predetermined region. The TV camera 93 images a two-dimensional image based on an image obtained by receiving light having transmitted through the light receiving side polarization plate 96. The image processing apparatus 94 detects the transparent object 90 based on projected light distribution of the image obtained by the TV camera 93. By having this configuration, the transparent object 90 can be detected. To that end, light polarized in a specific direction is projected to a predetermined region including the transparent object 90. Then, the light having transmitted through the predetermined region is further transmitted through the light receiving side polarization plate 96 that transmits only a specific polarized light. The light transmitted through the light receiving side polarization plate 96 is received by a CCD (Charge Coupled Device) of the TV camera 93. Based on the projected light distribution in an image obtained by the CCD, the transparent object 90 is detected.

However, according to the technique described in Patent Document 1, the transparent object is detected using birefringence (=double refraction) characteristics of the transparent object. Because of this feature, it may be difficult to detect a transparent flat plate having no birefringence characteristics such as a glass flat plate when the technique described in Patent Document 1 is applied.

On the other hand, as a technique of detecting an image of a plate-like object, Patent Document 2 discloses a surface inspection apparatus as illustrated in FIG. 2. As schematically illustrated in FIG. 2, the surface inspection apparatus forms an image indicating intensity distribution of polarized light by detecting polarized lights corresponding to different reflected lights from a surface of a steel plate 81 using line sensor cameras 82a through 82c.

[Patent Document 1] Japanese Laid-Open Patent Application No. 2002-98650
[Patent Document 2] Japanese Laid-Open Patent Application No. 09-166552

DISCLOSURE OF THE INVENTION

Problems to be Solved by the Invention (Problem 1: Position of Lighting Apparatus)

In the technique of Patent Document 1, it is necessary to dispose a lighting apparatus 97 and the light projecting side polarization plate 95 under the transparent object 90 with respect to the TV camera 93. However, in a practical production line and the like, there may be a process of cleaning the transparent object or the transparent flat plate. In such a process, droplets may be dropped downward. For safety reasons or the like, there may be a case where it is difficult to dispose the lighting apparatus 97 under the transparent object or the transparent flat plate.

Further, in the technique described in Patent Document 2, it may be required to dispose the light projecting section 83 and the polarizer so as to face each other with respect to the camera 82. Because of this necessity, when a transparent plane object is provided as the steel plate 81 to be inspected, it is required to irradiate light across the entire surface of the transparent plane object. Therefore, when plural transparent flat plate objects or a transparent flat plate object having a large size is to be inspected, it may become necessary to use a lighting apparatus having a large lighting area or to dispose a lighting apparatus to be separated from the object(s). As a result, the size of the system may become larger.

(Problem 2: Relocation from Tray to Detection Apparatus)

Further, in the technique described in Patent Document 1, when a tray is used or when a placing table and the tray are integrally used in a process, it may be necessary to relocate the transparent object to a transparent object detection apparatus first.

(Problem 3: Rotation Mechanism and Calibration Process are Necessary)

Further, in the technique described in Patent Document 1, it may be required to set the transmission polarization directions of the light projecting side polarization plate 95 and the light receiving side polarization plate 96 to be parallel to each other or orthogonal to each other. To that end, it may be required to rotate the light receiving side polarization plate 96 at every predetermined rotation pitch and measure respective images. Because of this feature, when, for example, the type of the transparent object 90 is changed, it takes time to respond to the change and time may be lost. Further, to add the rotation mechanism, the size of the apparatus becomes larger accordingly. Further, such a rotation mechanism may suffer from change over time (e.g., the center position may be shifted) in an environment such as in a manufacturing facility. Further, a moving part of the rotation mechanism may suffer from a problem due to being consumed. Therefore, appropriate maintenance may be required.

The present invention is made in light of the above problems, and may provide a transparent object detection system and a transparent flat plate detection system easily and accurately detecting a transparent object and a transparent flat plate, respectively and more particularly a transparent object detection system and a transparent flat place detection system detecting a transparent object regardless of the posture of the transparent object without disposing a lighting apparatus on a lower side, without requiring a calibration operation, and without having a dedicated rotation mechanism.

Further, the present invention may provide a transparent flat plate detection system easily and accurately detecting a transparent flat plate, more particularly a transparent flat plate detection system detecting a transparent flat plate regardless of the placing posture of the transparent flat plate without requiring a dedicated lighting apparatus, without requiring a calibration operation, and without having a rotation mechanism.

Means for Solving the Problems

In order to solve the above-described problems according to a first aspect of the present invention, there is provided a transparent body detection system including an image acquisition unit acquiring a vertical polarization image and a horizontal polarization image by acquiring an image of a first region, the image including a transparent body having characteristics in which a polarization direction of transmission light changes; a placing table on which the transparent body is to be placed; a polarization filter disposed opposite to the image acquisition unit across the placing table and at a position including a second region, an image of the second region including at least the transparent body in the first region and being acquired; and an image processing apparatus detecting the transparent body based on distribution of vertical/lateral polarization degree of a vertical/lateral polarization degree image based on the vertical polarization image and the horizontal polarization image.

By having this configuration, the vertical/lateral polarization degree image is acquired. Therefore, without depending on the direction of the polarization filter disposed under the transparent object, it may become possible to detect the polarization change of the transparent object, thereby enabling eliminating the calibration operation. Further, the rotation mechanism may not be necessary (Problem 3 may be resolved). Further, as the light to be transmitted to the transparent object, the light having been transmitted through the polarization filter 112 (i.e., light having a specific polarization direction) is used. It is not necessary to dispose a lighting apparatus right below the polarization filter 112 (Problem 1 may be resolved). Further, in a configuration where the placing table is disposed above the tray, the polarization filter is disposed between the placing table and the tray. It may not be necessary to perform an operation to relocate the transparent object from the placing table to a transparent object detection apparatus (Problem 2 may be resolved).

Further, according to a second aspect of the present invention, there is provided a transparent body detection system including an image acquisition unit acquiring a vertical polarization image and a horizontal polarization image by acquiring an image of a first region, the image including a transparent body having characteristics in which a polarization direction of transmission light changes; a placing table on which the transparent body is to be placed, the placing table reflecting light having a polarization direction substantially the same as a polarization direction of a third region, an image of the third region not including the transparent body and being acquired; a base disposed opposite to the image acquisition unit across the placing table and having characteristics where a gradation value of one of the vertical polarization image and the horizontal polarization image is higher than a gradation value of the other of the vertical polarization image and the horizontal polarization image; and an image processing apparatus detecting the transparent body based on distribution of the vertical/lateral polarization degree of a vertical/lateral polarization degree image based on the vertical polarization image and the horizontal polarization image.

By having the configuration, the vertical/lateral polarization degree image is acquired. Therefore, without depending on the direction of the polarization filter disposed under the transparent object, it may become possible to detect the polarization change of the transparent object, thereby enabling eliminating the calibration operation. Further, the rotation mechanism may not be necessary (Problem 3 may be resolved). Further, the system may be simplified and the cost of the system may be reduced.

Further, according to a third aspect of the present invention, in the transparent body detection system according to the first or the second aspect of the present invention, the image processing apparatus detects a position and a posture of the detected transparent body.

Further, according to a fourth aspect of the present invention, in the transparent body detection system according to the third aspect of the present invention, the transparent body detection system further includes a robot hand; and a robot controller controlling the robot hand, so that the robot controller causes the robot hand to move based on the position of the detected transparent body and pick up the transparent body based on the posture of the detected transparent body.

Further, according to a fifth aspect of the present invention, in the transparent body detection system according, to the third or the fourth aspect of the present invention, the image processing apparatus determines an existence region of the transparent body based on the position and the posture of the detected transparent body, compares two or more existence regions of the transparent body, and detects a fault in a shape of the transparent body.

Further, according to a sixth aspect of the present invention, in the transparent body detection system according to any one of third through fifth aspects of the present invention, the image processing apparatus determines an existence region of the transparent body based on the position and the posture of the detected transparent body and detects a fault in appearance of the transparent body based on luminance distribution of a monochrome luminance image based on the vertical polarization image and the horizontal polarization image.

Further, according to a seventh aspect of the present invention, in the transparent body detection system according to any one of the third through the sixth aspects of the present invention, the image processing apparatus determines an existence region of the transparent body based on the position and the posture of the detected transparent body and detects at least one of character information and design pattern information based on luminance distribution of a monochrome luminance image based on the vertical polarization image and the horizontal polarization image, the character information and design pattern information being formed on a surface of the transparent body.

Further, according to an eighth aspect of the present invention, in the transparent body detection system according to any one of the third through the seventh aspects of the present invention, the transparent body is transparent foreign matter to be mixed in an empty bottle or in a bottle in which is filled with transparent fluid, and the image processing apparatus determines whether the transparent foreign matter is mixed in the empty bottle or in the bottle which is filled with transparent fluid based on the distribution of the vertical/lateral polarization degrees of the vertical/lateral polarization degree image based on the vertical polarization image and the horizontal polarization image.

Further, according to a ninth aspect of the present invention, there is provided a transparent flat plate detection system including an image acquisition unit acquiring a vertical polarization image and a horizontal polarization image by acquiring, an image of a region including a transparent flat plate, the image being acquired with a predetermined angle with respect to a normal line of a flat surface part of the transparent flat plate; a placing table on which the transparent flat plate is to be placed; a reflection surface disposed on an optical path passing through the transparent flat plate and the image acquisition unit and under the placing table; a light shielding plate disposed so as to face the image acquisition unit with respect to the normal line of the flat surface part of the transparent flat plate and block light so as to prevent mirror reflection light from the flat surface part of the transparent flat plate from being incident on the image acquisition unit; and an image processing apparatus detecting the transparent flat plate based on distribution of the vertical/lateral polarization degree of a vertical/lateral polarization degree image based on the vertical polarization image and the horizontal polarization image.

By having this configuration, the vertical/lateral polarization degree image data are acquired. Therefore, without depending on the direction of the polarization filter disposed under the transparent flat plate, it may become possible to detect the polarization change of the transparent flat plate, thereby enabling eliminating the calibration operation. Further, the rotation mechanism may not be necessary (Problem 3 may be resolved). Further, the mirror reflection light from the transparent flat plate is not incident on the image acquisition unit and the light transmitted through the transparent flat plate is used. Therefore, it is not necessary to provide a dedicated lighting apparatus, and even under fluorescent light, it may become possible to detect the transparent flat plate (Problem 1 may be resolved). Further, in a state where the placing table is disposed above the tray and the transparent flat plate is placed on the placing table or in a state that the transparent flat plate is placed directly on the placing table, it may become possible to detect the transparent flat plate (Problem 2 may be resolved).

Further, according to a tenth aspect of the present invention, there is provided a transparent flat plate detection system including an image acquisition unit acquiring a vertical polarization image and a horizontal polarization image by acquiring an image of a region including a transparent flat plate, the image being acquired with a predetermined angle with respect to a normal line of a flat surface part of the transparent flat plate; a reflection surface disposed so as to face the image acquisition unit with respect to the normal line of the flat surface part of the transparent flat plate and having an elevation angle so that mirror reflection light from the flat surface part of the transparent flat plate is incident on the image acquisition unit; and an image processing apparatus detecting the transparent flat plate based on distribution of the vertical/lateral polarization degree of a vertical/lateral polarization degree image based on the vertical polarization image and the horizontal polarization image.

By having this configuration, the vertical/lateral polarization degree image data are acquired. Therefore, without depending on the direction of the polarization filter disposed under the transparent flat plate, it may become possible to detect the polarization change of the transparent flat plate, thereby enabling eliminating the calibration operation. Further, the rotation mechanism may not be necessary (Problem 3 may be resolved). Further, the reflection surface is disposed so as to face the image acquisition unit so that the mirror reflection light from the flat surface part of the transparent flat plate is incident on the image acquisition unit. Therefore, it is not necessary to provide a dedicated lighting apparatus, and even under the fluorescent light, it may become possible to detect the transparent flat plate (Problem 1 may be resolved). Further, for example, in a state where the placing table is disposed above the tray and the transparent flat plate is placed on the placing table or in a state where the transparent flat plate is placed directly on the placing table, it may become possible to detect the transparent flat plate regardless of the placing state of the transparent flat plate (Problem 2 may be resolved).

Further, according to an eleventh aspect of the present invention, in the transparent flat plate detection system according to the ninth or the tenth aspect of the present invention, the image processing apparatus detects a position and a posture of the detected transparent flat plate.

Further, according to a twelfth aspect of the present invention, the transparent flat plate detection system according to the eleventh aspect of the present invention further includes a robot hand; and a robot controller controlling the robot hand, so that the robot controller causes the robot hand to move based on the position of the detected transparent flat plate and pick up the transparent flat plate based on the posture of the detected transparent flat plate.

Further, according to a thirteenth aspect of the present invention, in the transparent flat plate detection system according to the eleventh or the twelfth aspect of the present invention, the image processing apparatus determines an existence region of the transparent flat plate based on the position and the posture of the detected transparent flat plate, compares two or more existence regions of the transparent flat plate, and detects a fault in the shape of the transparent flat plate.

Further, according to a fourteenth aspect of the present invention, in the transparent flat plate detection system according to any one of the eleventh through the thirteenth aspects of the present invention, the image processing apparatus determines an existence region of the transparent flat plate based on the position and the posture of the detected transparent flat plate and detects a fault in appearance of the transparent flat plate based on luminance distribution of a monochrome luminance image based on the vertical polarization image and the horizontal polarization image.

Further, according to a fifteenth aspect of the present invention, in the transparent flat plate detection system according to any one of the eleventh through the fourteenth aspects of the present invention, the image processing apparatus determines an existence region of the transparent flat plate based on the position and the posture of the detected transparent flat plate and detects at least one of character information and design pattern information based on luminance distribution of a monochrome luminance image based on the vertical polarization image and the horizontal polarization image, the character information and design pattern information being formed on a surface of the transparent flat plate.

Effects of the Present Invention

According to an embodiment of the present invention, it may become possible to easily and accurately detect a transparent body and a transparent flat plate.

BRIEF DESCRIPTION OF THE DRAWINGS

FIG. 20A is a drawing illustrating a monochrome luminance image of an example of an acquired image of a transparent flat plate;

FIG. 20B is a drawing illustrating a vertical/lateral polarization degree image of the example;

FIG. 30A is a drawing illustrating a monochrome luminance image of another example of an acquired image of a transparent flat plate; and FIG. 30B is a drawing illustrating a vertical/lateral polarization degree image of the example.

DESCRIPTION OF THE REFERENCE NUMERALS

1A: TRANSPARENT OBJECT DETECTION SYSTEM
1B: TRANSPARENT FLAT PLATE DETECTION SYSTEM
11A: TRANSPARENT OBJECT PLACING SECTION
11B: TRANSPARENT FLAT PLATE PLACING SECTION
12: CAMERA (IMAGE ACQUISITION UNIT)
13: IMAGE PROCESSING APPARATUS
14: MONITOR
15: ROBOT CONTROLLER
16: ROBOT HAND
20a, 20b: POLARIZATION FILTER
21: OPTICAL SYSTEM
22: LENS ARRAY
23: LIGHT SHIELDING SPACER
24: POLARIZATION FILTER
25: SPACER
26: SOLID-STATE IMAGING UNIT
27a, 27b: OPTICAL AXIS
28a, 28b: LENS
29a, 29b: APERTURE
30a, 30b: POLARIZER REGION
31: APERTURE
32: SUBSTRATE
33a, 33b: SOLID-STATE IMAGING DEVICE
34: HALF MIRROR BOX
35: MIRROR
36: VERTICAL POLARIZATION FILTER
37: HORIZONTAL POLARIZATION FILTER
38, 39: CCD
40: LIGHT RECEIVING DEVICE ARRAY
41: POLARIZATION FILTER REGION (VERTICAL)
42: POLARIZATION FILTER REGION (LATERAL)
43: MISSING PORTION
44: BURR
45: BLEMISH
101: FLUORESCENT LIGHT
102: LIGHT SHIELDING PLATE
103: REFLECTION PLATE
111: TRAY
112: POLARIZATION FILTER
113: PLACING TABLE
114A: TRANSPARENT OBJECT
114B: TRANSPARENT FLAT PLATE
115: REFLECTION SURFACE
131: A/D CONVERTER
132: MEMORY
133: DISPLAY CONTROL SECTION
135: CPU

BEST MODE FOR CARRYING OUT THE INVENTION

In the following, exemplary configurations according to embodiments of the present invention are described with reference to FIGS. 3 through 18.

Transparent Object Detection System

A transparent object detection system 1A according to an embodiment of the present invention includes an image acquisition unit (camera 12), a placing table 113, a polarization filter 112, and an image processing apparatus 13. The image acquisition unit (camera 12) acquires a vertical polarization image and a horizontal polarization image by acquiring an image of a first region, the image including a transparent object 114A having characteristics in which a polarization direction of transmission light changes. The placing table 113 is provided so that the transparent object 114A is placed on the placing table 113. The polarization filter 112 is disposed at the position in a manner such that the polarization filter 112 faces the image acquisition unit (camera 12) across the placing table 113. Further, the polarization filter 112 is disposed at a position in a manner such that, when an image of a second region is acquired, the acquired image includes at least the transparent object 114A included in the first region, the second region being included in the polarization filter 112. The image processing apparatus 13 detects the transparent object 114A based on the distributions of vertical/lateral polarization degree of a vertical/lateral polarization degree image based on the vertical polarization image and the horizontal polarization image.

Figure 1:
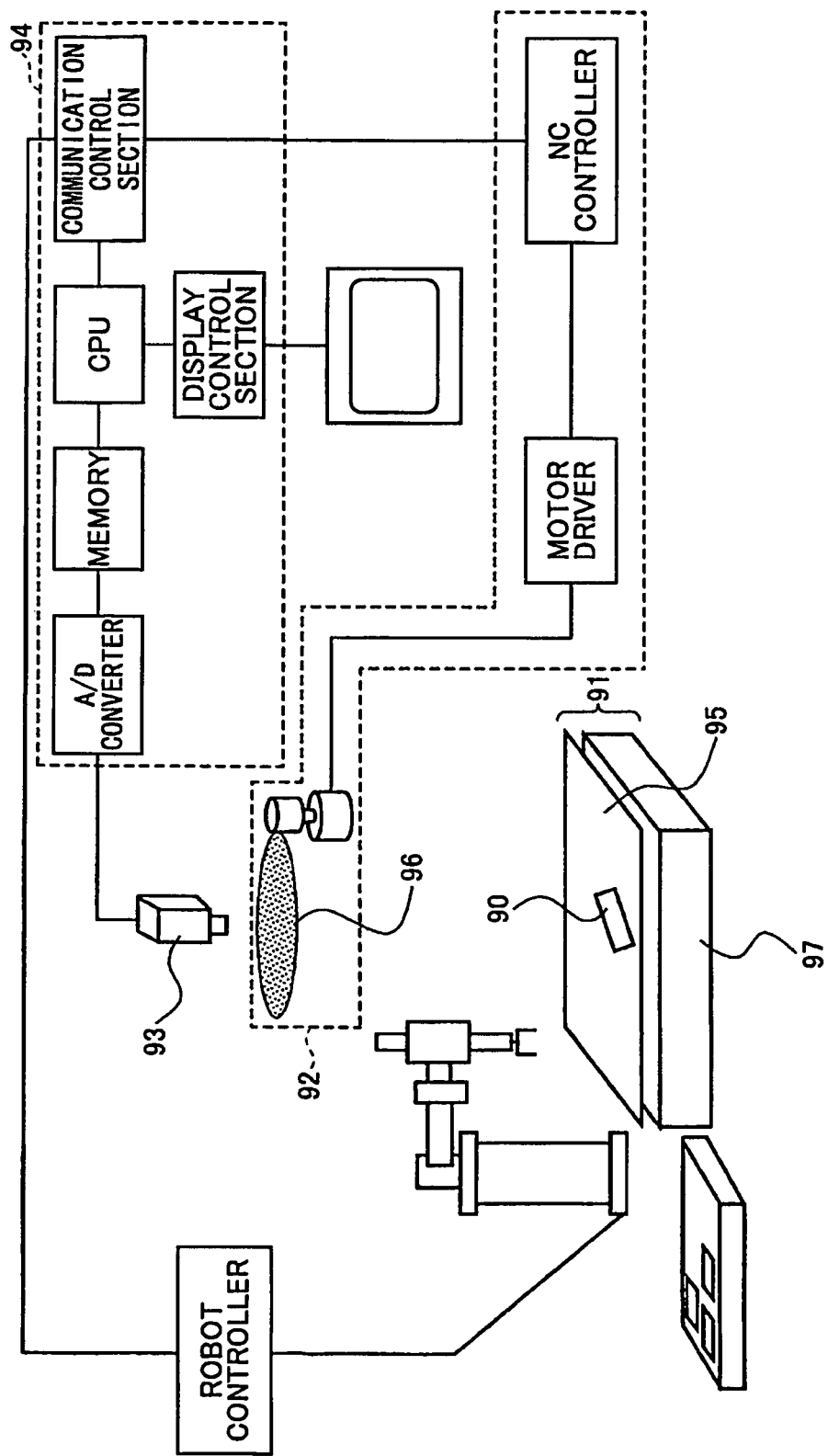
FIG. 1 is a drawing illustrating an example of a conventional transparent body detection system.
Figure 2:
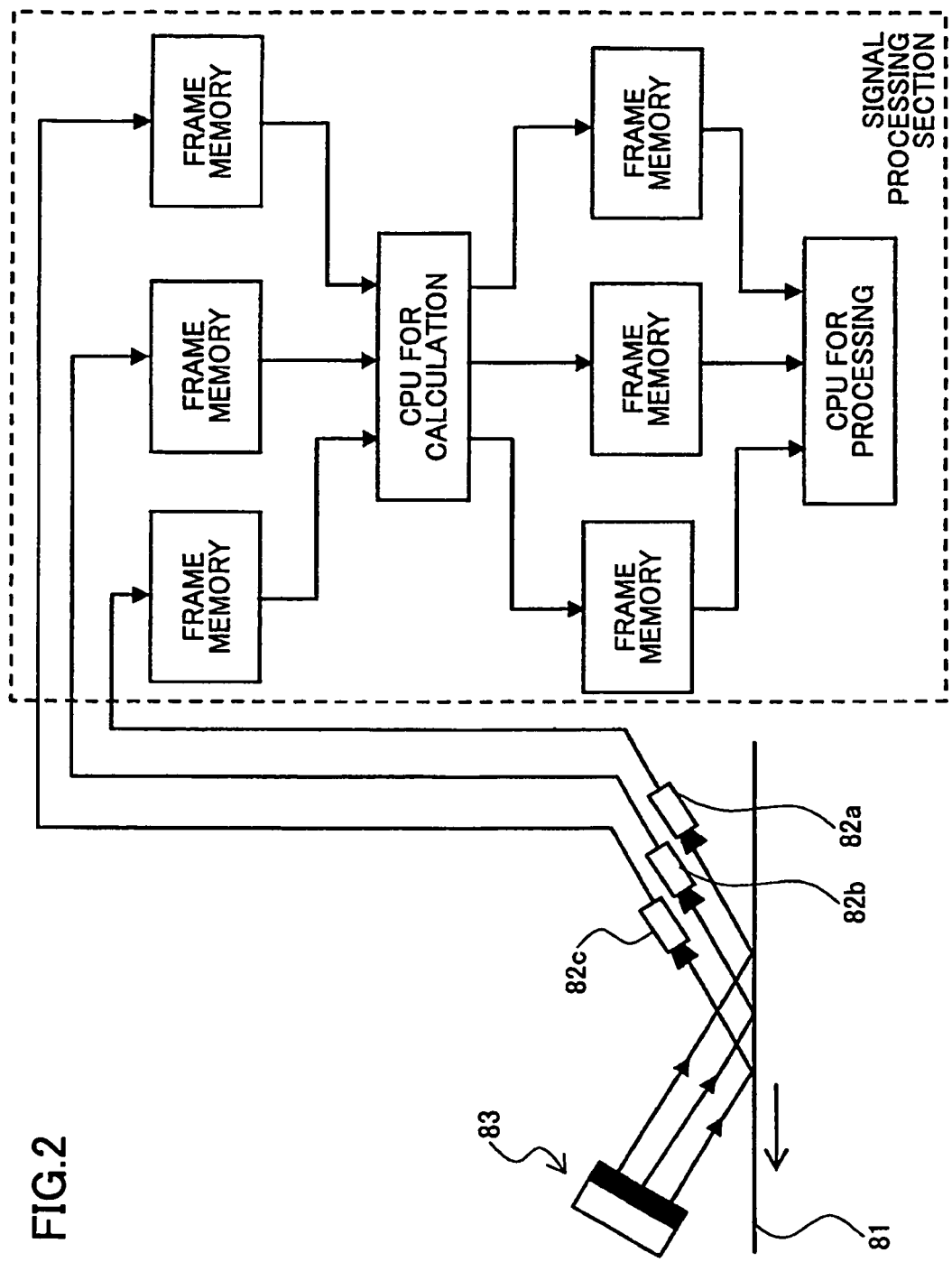
FIG. 2 is a drawing illustrating an example of a conventional surface inspection apparatus.
Figure 3:
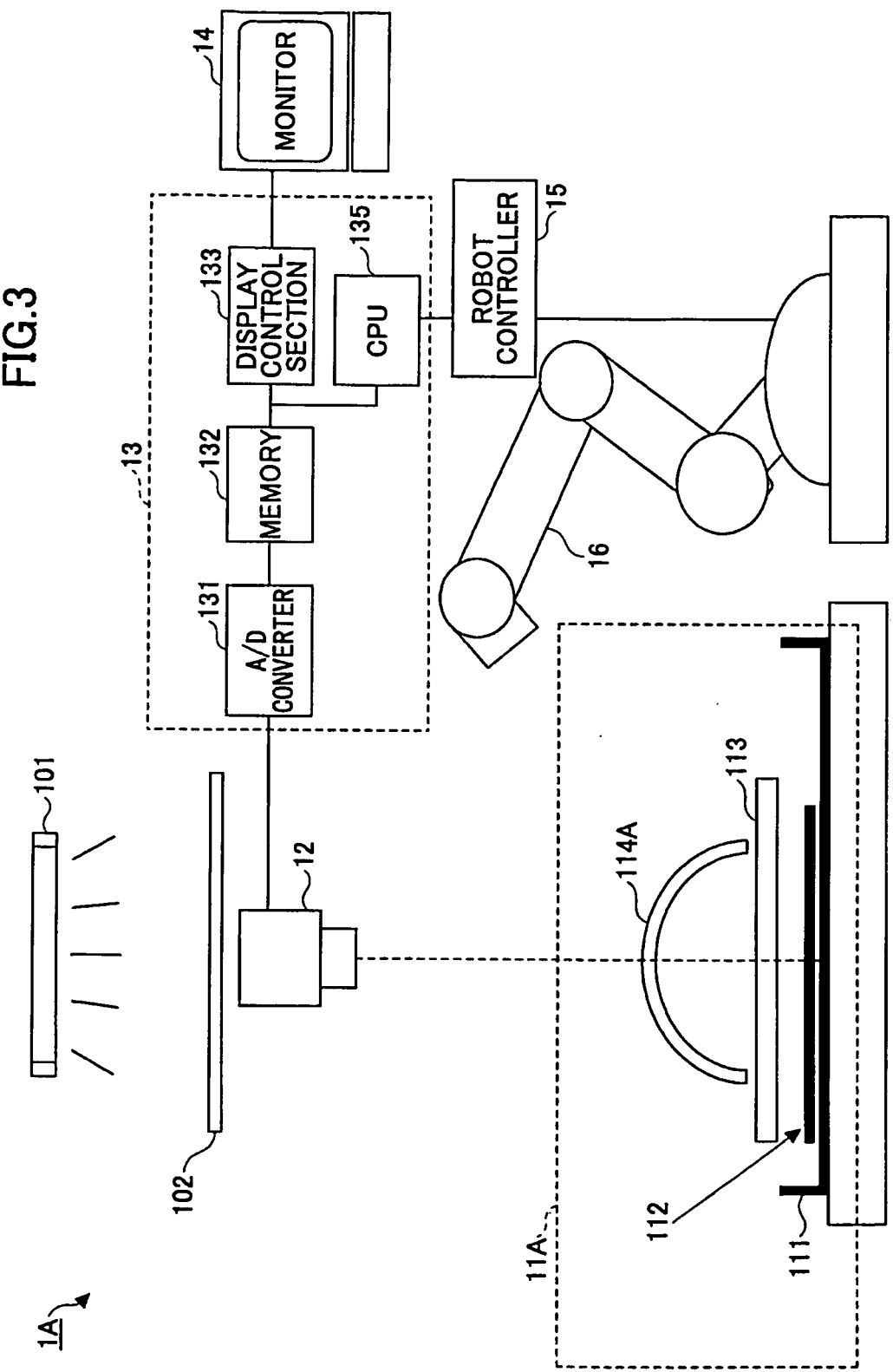
FIG. 3 is a schematic drawing illustrating a transparent object detection system according to an embodiment of the present invention.

FIG. 3 schematically illustrates a configuration of the transparent object detection system 1A. The transparent object detection system 1A includes a transparent object placing section 11A, the camera 12, the image processing apparatus 13, a monitor 14, a robot controller 15, and a robot hand 16. The camera 12 acquires both a monochrome luminance image and a vertical/lateral polarization degree image.

For example, the transparent object detection system 1A is installed in a manufacturing facility and disposed under indoor lighting such as a fluorescent light 101. Further, the transparent object detection system 1A is disposed in a manner such that the placing table 113 of the transparent object placing section 11A is parallel to the ground, and the camera 12 acquires an image of the transparent object 114A along the normal direction of the placing table 113. Further, a light shielding plate 102 is disposed between the camera 12 and the indoor lighting (e.g., the fluorescent light 101) so that the indoor lighting cannot directly irradiate the transparent object 114A. However, the light from the overhead fluorescent light 101 may be shielded partially. As the light shielding plate 102, for example, a color plastic plate may be used. However, any other plate or the like having sufficient light shielding capability may alternatively used. By disposing the light shielding plate 102, unnecessary reflection light on the surface of the transparent object 114A may be removed, thereby enabling improving detection accuracy of the transparent object 114A.

The transparent object placing section 11A includes the placing table 113 and the polarization filter 112. The placing table 113 is provided so that the transparent object 114A is placed on the placing table 113. The polarization filter 112 is disposed at a position in a manner such that the polarization filter 112 faces the image acquisition unit (camera 12) across the placing table 113 and includes a range of the region (the second region) including at least the transparent object 114A, so that an image of the second region may be acquired. A tray 111 is disposed under the polarization filter 112. The tray 111 is provided so as to receive droplets from the transparent object 114A after, for example, a cleaning process of the transparent object 114A.

Further, the placing table 113 has a net (mesh) structure in a manner such that a mesh (pattern) occupation rate of the net (mesh) structure is determined so that light reflected from the tray 111 and then transmitted through the polarization filter 112 can be sufficiently transmitted through the transparent object 114A. Specifically, it is preferable that the mesh (pattern) occupation rate is approximately 5% of the region of the transparent object 114A. Further, it is preferable that the wires of the mesh (pattern) be thin, so that the width of the wires is equal to or less than 5% of the size of the transparent object 114A. By having the size (structure) described above, the size of the region where polarized light transmits through the transparent object 114A may be increased and the size of the background region may also be increased, thereby enabling improving the accuracy of detecting the edge of the transparent object 114A.

As the polarization filter 112, it is preferable to use a filter having an organic film structure. By using such an organic film, it may become possible to have a larger area at less cost, thereby enabling reducing the cost of the transparent object detection system 1A. Further, such an organic film has elasticity, therefore it may become possible to easily paste the film on the tray 111 with sealing material even when the tray 111 has a moderate concavo-convex portion.

Further, in this embodiment, a case is described where the tray 111 is disposed. However, it may be sufficient when the polarization filter 112 is disposed under the placing table 113. Therefore, for example, a floor may be disposed under the polarization filter 112. Further, the polarization filter 112 is provided for the purpose of irradiating a specific polarized light onto the transparent object 114A. Therefore, as long as the purpose is attained, any appropriate filter may alternatively be used. For example, instead of using a transmissive polarization filter, a reflective polarization filter may be used. As the reflective polarization filter, for example, a resin-shaped wiregrid-type filter is known.

Further, in this embodiment, a case is described where the transparent object 114A that has a hemispherical shape and that has been formed by injection molding a polycarbonate resin is used. It is known that a transparent object 114A made of such as glass does not change polarization characteristics and that a transparent object 114A made of resin changes the polarization characteristics or does not change the polarization characteristics depending on the forming methods. However, when, for example, polycarbonate resin is used as the transparent object 114A, the characteristics in which the polarization direction changes are developed when the transparent object 114A is formed based on the injection molding method or the like. This is why the transparent object 114A that is made of polycarbonate resin and that has been formed by injection molding or the like is herein used.

The camera 12 used in this embodiment acquires a luminance monochrome image and a vertical/lateral polarization degree image as well. Pixel signals of two-dimensional acquired images are output (transmitted) from the respective sensors in the camera 12 to the image processing apparatus 13.

The image processing apparatus 13 includes an A/D converter 131, a memory 132, a display control section 133, a CPU 135, and a communication control section (not shown). The A/D converter 131 A/D converts the pixel signals into digital binary values or multiple values. The memory 132 stores those values. The display control section 133 controls the display of the monitor 14. The communication control section performs communication control on control signals for the robot controller 15. The CPU 135 performs various image processing and calculations based on the programs stored in a ROM (not shown) or the like.

The image processing apparatus 13 detects the position, the posture, the size (existence region) and the like of the transparent object 114A based on the images acquired by the camera 12 by using projected light distribution (bright-dark distribution) of the image data stored in the memory 132.

Further, in the image processing apparatus 13, the display control section 133 causes the monitor 14 to display the results of the obtained position, posture and the like of the transparent object 114A. Further, in the image processing apparatus 13, a control signal obtained based on the position, the posture and the like of the transparent object 114A is transmitted to the robot controller 15.

The monitor 14 is a display apparatus such as a LCD or a CRT. The robot controller 15 controls the robot hand 16 based on the control signal transmitted from the image processing apparatus 13. The robot hand 16 picks up the transparent object 114A placed on the placing table 113 and arranges and stores the picked-up transparent object 114A in a storage section (not shown) such as tray disposed under the control of the robot controller 15.

Image Acquisition Unit

Next, a configuration of the camera 12 serving as an image acquisition unit acquiring the vertical/lateral polarization degree image is described. The camera 12 acquires an image of a surrounding area including the transparent object 114A, the image having a megapixel size or the like, by using an imaging acquisition device (light receiving device) such as a CCD (Charge-Coupled Device) or a CMOS (Complementary Metal Oxide Semiconductor). The camera 12 used in the transparent object detection system 1A according to this embodiment of the present invention acquires not only a luminance image but also a polarization image. In the following, the camera 12 for acquiring (forming) the polarization image is described.

First Embodiment of Image Acquisition Unit (Camera)

Figure 4:
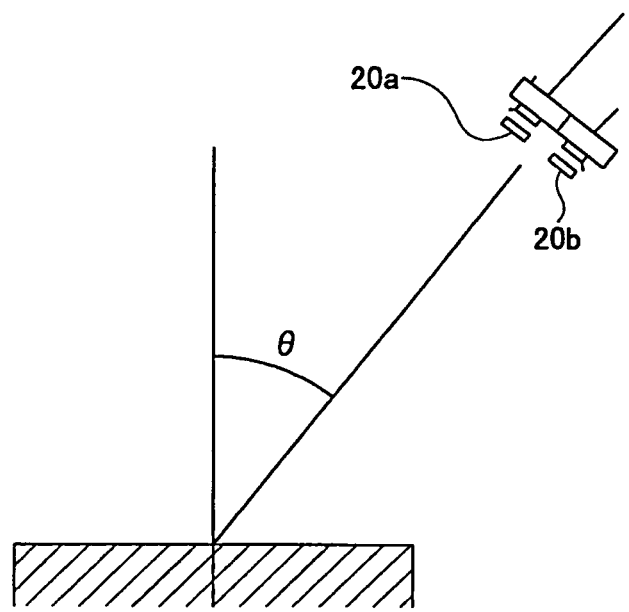
FIG. 4 is a drawing illustrating a first exemplary configuration of an image acquisition unit.

In this embodiment, as schematically illustrated in FIG. 4, the camera 12 includes a first camera and a second camera, the first camera being for acquiring a vertical polarization image using a polarization filter 20a disposed at a position where a polarization light polarized in the vertical direction transmits, the second camera being for acquiring a lateral polarization image using a polarization filter 20b disposed at a position where a polarization light polarized in the lateral direction transmits. By having this structure, the camera 12 may acquire both the vertical polarization image and the lateral polarization image at the same time unlike a conventional camera that does not acquire those images at the same time and without rotating the polarization filters which may cause time delay between the acquired images.

Further, unlike a known stereo method, the first and second cameras may be disposed close to each other. Recently, there has been a strong demand for reducing the size of the apparatus. As a structure further reducing the size of the camera in FIG. 4, it is preferable that, as illustrated in FIG. 5, the camera 12 has a structure acquiring the images using a single light receiving device via the lens array and the polarizer filter array.

Figure 5:
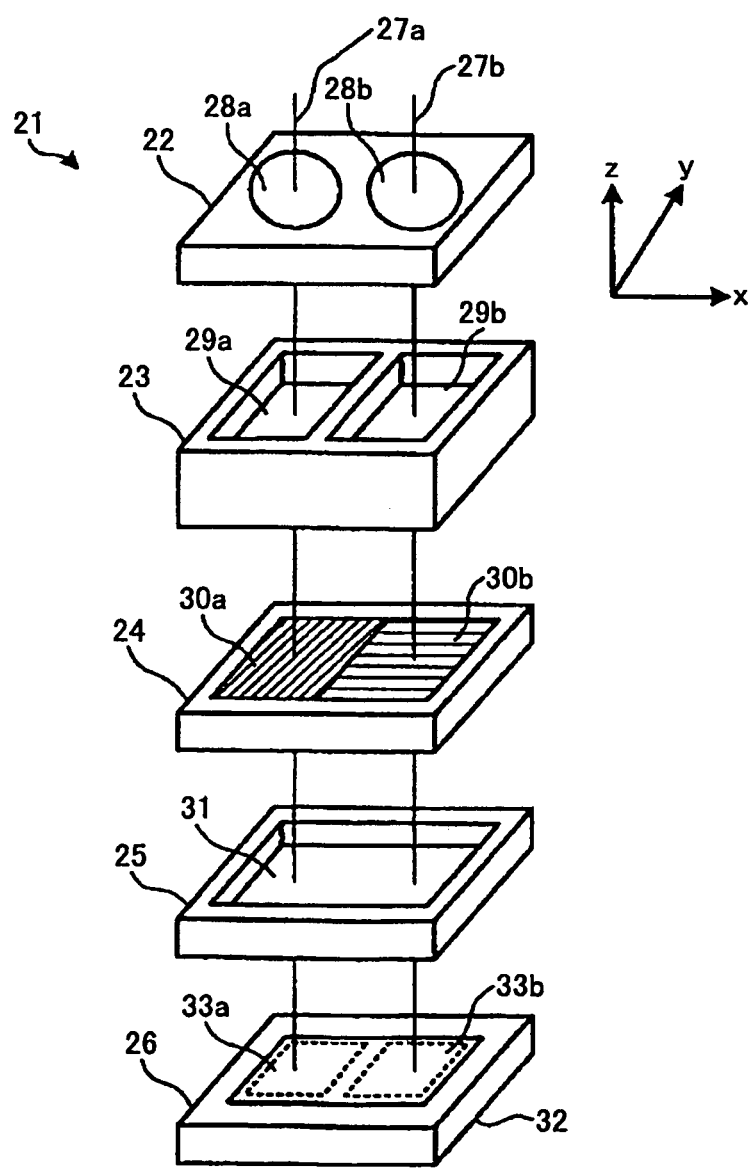
FIG. 5 is a drawing illustrating a second exemplary configuration of an image acquisition unit.

FIG. 5 schematically illustrates a configuration of an optical system 21 of the camera 12. The optical system 21 includes two optical systems, one optical system being for acquiring the vertical polarization image, the other optical system being for acquiring the lateral polarization image. Further, a lens array 22, a light shielding spacer 23, a polarization filter 24, a spacer 25, and a solid-state image acquisition unit 26 are formed and laminated to each other.

The lens array 22 includes two lenses 28a and 28b. Two lenses 28a and 28b are made of respective single lenses having the same shape such as a hemispherical lens and the like. The two lenses 28a and 28b have respective optical axes 27a and 27b parallel to each other. Further, the two lenses 28a and 28b are disposed on the same plane. Namely, when the direction parallel to the optical axes 27a and 27b is defined as Z direction, one direction perpendicular to the Z direction is defined as the X direction, and the direction perpendicular to the Z direction and the X direction is defined as the Y direction, the two lenses 28a and 28b are disposed on the same XY plane.

The light shielding spacer 23 has two apertures 29a and 29b, and is disposed opposite to an object-of-shooting side (side where an object to be imaged is disposed) with respect to the lens array 22. The apertures 29a and 29b are through holes having a predetermined size and having centers disposed on the respective optical axes 27a and 27b. Further, an optical anti-reflective treatment is performed on the inner walls of the apertures 29a and 29b, the optical anti-reflective treatment including black coating, a rough surface, a matte finish or the like.

The polarization filter 24 includes two polarizer regions 30a and 30b having the respective polarization planes being different by 90 degrees from each other. The polarization filter 24 is disposed opposite to the lens array 22 with respect 15, to the light shielding spacer 23. The polarizer regions 30a and 30b are disposed in a manner such that the centers of the polarizer regions 30a and 30b are disposed on the optical axes 27a and 27b, respectively, and further disposed on an XY plane. Each of the polarizer regions 30a and 30b is provided for polarizing unpolarized light in which the electric field and the magnetic field are vibrated in unspecific directions so as to transmit only a linearly-polarized light having a vibration component along the specified polarization plane direction.

The spacer 25 has a rectangular frame shape having an aperture 31 which is a through hole including a region corresponding to the polarizer regions 30a and 30b of the polarization filter 24. The spacer 25 is disposed opposite to the light shielding spacer 23 with respect to the polarization filter 24.

The solid-state image acquisition unit 26 includes two solid-state image acquisition devices 33a and 33b mounted on a substrate 32 having a signal processing section (not shown). The solid-state image acquisition unit 26 is disposed opposite to the polarization filter 24 with respect to the spacer 25. Imaging regions of the solid-state image acquisition devices 33a and 33b are disposed in a manner such that the centers of the imaging regions of the solid-state image acquisition devices 33a and 33b are disposed on the optical axes 27a and 27b, respectively, and are disposed on an XY plane. The imaging regions are where images of an object to be imaged are formed. When each of the solid-state image acquisition devices 33a and 33b senses (acquires) a black and while image, no color filter is included. On the other hand, when each of the solid-state image acquisition devices 33a and 33b senses (acquires) a color image, a color filter is disposed at a previous stage.

Second Embodiment of Image Acquisition Unit (Camera)

Figure 6:
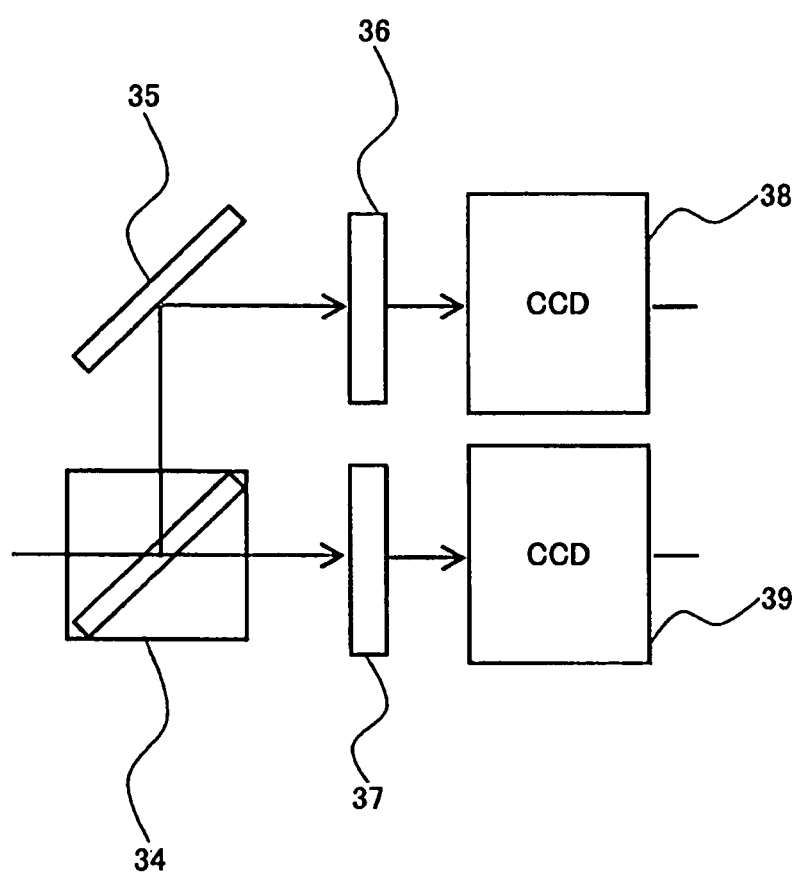
FIG. 6 is a drawing illustrating a third exemplary configuration of an image acquisition unit.

In this embodiment, as schematically illustrated in FIG. 6, it is preferable to use a camera 12 in which a single imaging lens (or plural lenses on the same axis) is used to acquire (form) an image, and at a subsequent stage, an image is divided into the vertical polarization image and the lateral (horizontal) polarization image to form the vertical/lateral polarization degree image.

To acquire the vertical polarization image and the lateral polarization image, as schematically illustrated in FIG. 6, the camera 12 includes a half mirror box 34, a mirror 35, a vertical polarization filter 36, a horizontal polarization filter 37, and CCDs 38 and 39. The half mirror box 34 has transmissivity of 1:1 (i.e., 50% of light is transmitted and 50% of the light is reflected). The CCDs 38 and 39 are provided for acquiring visual field images through the vertical polarization filter 36 and the horizontal polarization filter 37, respectively. The camera 12 in the first embodiment can acquire both the vertical polarization image and the lateral polarization image but parallax may occur between the acquired images. On the other hand, the camera 12 in the second embodiment does not cause parallax because the same imaging optical system (lens) is used for acquiring the images. Because of this feature, a detection region may become smaller and it may become no longer necessary to calibrate the parallax and the like.

Instead of using the half mirror box 34, a polarization beam splitter reflecting lateral polarization light and transmitting vertical polarization light may be used. When the polarization beam splitter is used, it becomes no longer necessary to have the vertical polarization filter 36 and the horizontal polarization filter 37. Further, it may become possible to simplify the configuration of the optical system and improve the light-use efficiency.

Third Embodiment of Image Acquisition Unit (Camera)

Figure 7:
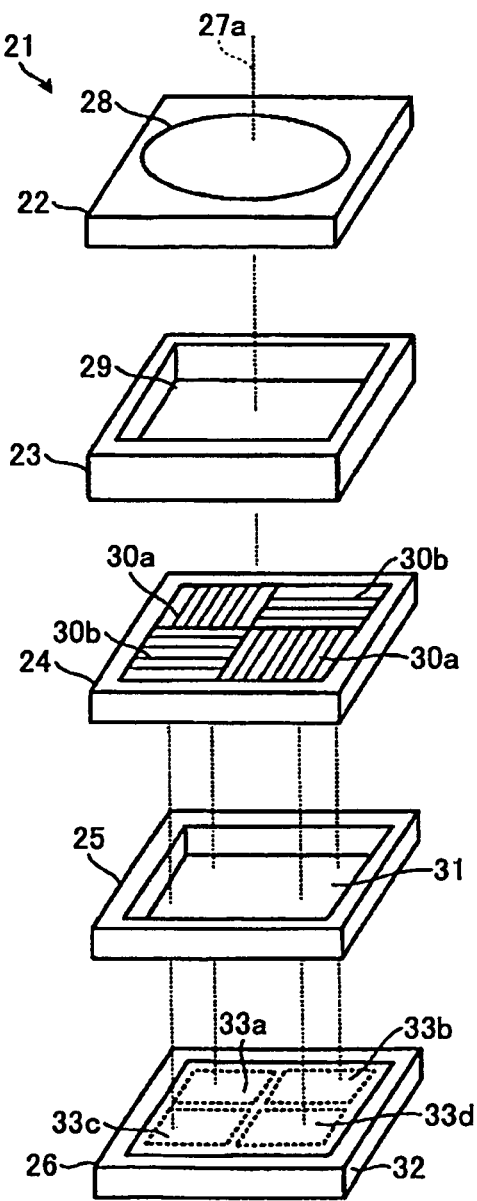
FIG. 7 is a drawing illustrating a first exemplary configuration of an image acquisition unit.

In this embodiment, as schematically illustrated in FIG. 7, it is preferable to use a camera 12 in which a single imaging lens (or plural lenses in the same axis) is used to acquire (form) an image, and at a subsequent stage of the lens, there is disposed a region-dividing-type polarization filter 24 including one or more polarizer regions transmitting only vertical polarization light and one or more polarizer regions transmitting only horizontal (lateral) polarization light. In this case, to form the polarizer regions, the region-dividing-type polarization filter 24 having the explicit boundaries between the regions may be formed by using the wiregrid method based on a metal having a fine concavo-convex shape or the autocloning-type photonic crystal method.

When the camera 12 in the second embodiment is used, the vertical polarization light and the lateral polarization light are obtained by separating light using a prism. Because of this feature, the size of the optical system may become larger, and two light receiving devices are required. On the other hand, when the camera 12 in the third embodiment is used, both the lateral polarization image and the vertical polarization image are acquired by the optical system having the same axis of the imaging lens.

Figure 8:
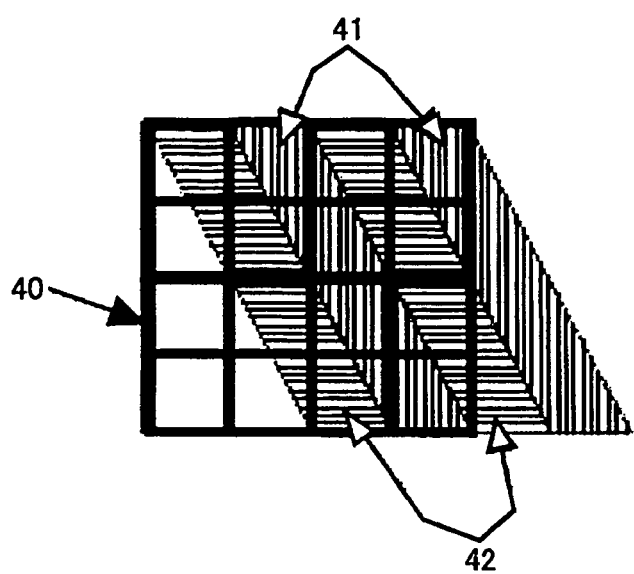
FIG. 8 is a drawing illustrating a region division type filter.

In this embodiment, a configuration of the region-dividing-type polarization filter 24 is not limited to a configuration in which there is one-to-one correspondence between each pixel of the light receiving device and the corresponding filter. For example, it is preferable that the region-dividing-type polarization filter 24 have the configuration as schematically illustrated in FIG. 8. In the configuration of FIG. 8, squares arranged in both vertical and lateral directions denote light receiving parts of the respective light receiving devices (i.e., a light receiving device array 40). Two types of tilted bands denote the polarization filter regions in vertical and lateral directions 41 and 42. Each of the polarization filter regions 41 and 42 has a band shape. The width of the band shape corresponds to one pixel that is same as the width of one light receiving device. Further, a tilt value of the boundaries between the polarization filter regions 41 and 42 of the band shape is two (2), namely the angle of the tilt is determined by a one-pixel width in the lateral direction and a two-pixel length in the vertical direction (when it proceeds one pixel in the lateral direction, it also proceeds two pixels in the vertical direction).

By using such a specific disposal pattern of the filters and the signal processing techniques, it may become possible to re-create filter transmission images across the entire screen even when the accuracy of alignment when the imaging device array and the region-dividing-type polarization filters are joined is not sufficient, and it may become possible to realize such an image acquisition apparatus at low cost.

As described above, the camera 12 in the transparent object detection system 1A according to this embodiment of the present invention acquires a polarization image. Further, preferably, an image of the transparent object 114A can be acquired in real time, and the acquired image is supplied to the image processing apparatus 13.

Detection of Transparent Object

The camera 12 in the transparent object detection system 1A according to an embodiment of the present invention uses (detects) birefringence (double refraction) that occurs especially in a plastic transparent object. In an object such as a film and a substrate, the birefringence may occur as a result of distortion or stress, and optical anisotropy and phase difference may occur due to slight anisotropy in the configuration. When light polarized in a specific direction is incident onto such an object, the polarization direction of the light transmitted through the object may be changed. The camera 12 detects the change.

Case where Polarization Light Transmission Direction of Polarization Filter is P Direction As described above, the camera 12 acquires the vertical/lateral polarization degree image. For example, the vertical/lateral polarization degree image has gradations (gradation values) (e.g., 256 gradations) in the polarization direction from horizontal component (S component) to vertical component (P component). In this case, for example, when light having the S component is incident, bright gradation is displayed. On the other hand, when light having the P component is incident, dark gradation is displayed.

Figure 9A:
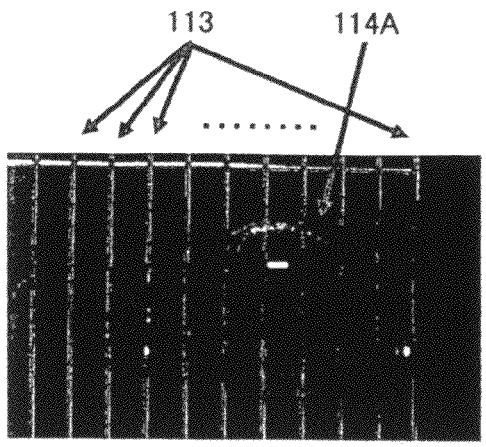
FIG. 9A is a drawing illustrating a monochrome luminance image of a first example of an acquired image of a transparent object.
Figure 9B:
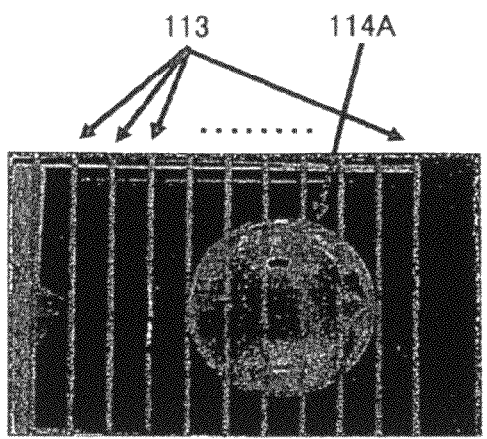
FIG. 9B is a drawing illustrating a vertical/lateral polarization degree image of the first example.

FIGS. 9A and 9B illustrate examples of the images acquired by the camera 12 in disposition so that the transmission direction of the polarization filter denotes the P component. FIG. 9A illustrates an example of the monochrome luminance image, and FIG. 9B illustrates an example of the vertical/lateral polarization degree image.

As illustrated in FIG. 9B, the vertical/lateral polarization degree of the background part where light does not transmit through the transparent object 114A is displayed in dark gradation. On the other hand, the vertical/lateral polarization degree of the region where light transmitted through the transparent object 114A is displayed in bright gradation because of the change in the polarization direction of the transmission light caused by birefringence. On the other hand, in the monochrome luminance image of FIG. 9A, only the edge portion of the transparent object 114A is slightly displayed in white. Further, in the image processing, it appears to be difficult to distinguish the transparent object 114A from the placing table 113. As described above, when the vertical/lateral polarization degree image is used, the contrast between the region of the transparent object 114A and the rest of the region may become clear, namely it may become possible to explicitly distinguish the region of the transparent object 114A from the rest of the region. Because of this feature, it may become possible to extract the region of the transparent object 114A based on the following image processing procedure (flow).

Figure 10A:
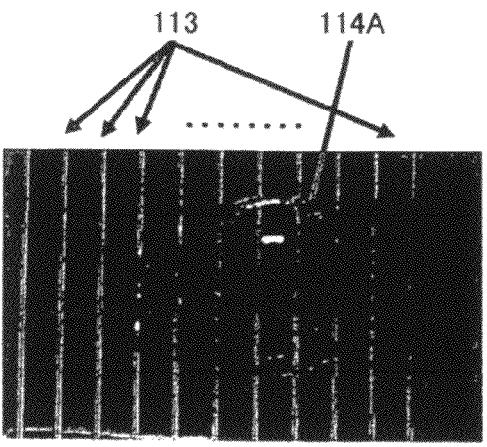
FIG. 10A is a drawing illustrating a monochrome luminance image of a second example of an acquired image of a transparent object.
Figure 10B:
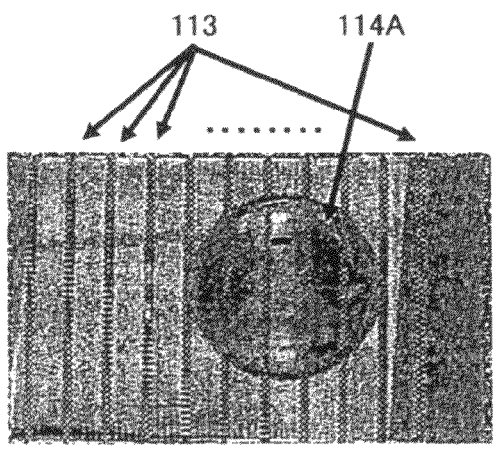
FIG. 10B is a drawing illustrating a vertical/lateral polarization degree image of the second example.

Case where Polarization Light Transmission Direction of Polarization Filter is S Direction FIGS. 10A and 10B illustrate examples of the images acquired by the camera 12 in disposition so that the transmission direction of the polarization filter denotes the S component. FIG. 10A illustrates an example of the monochrome luminance image and FIG. 10B illustrates an example of the vertical/lateral polarization degree image.

As illustrated in FIG. 10B, the vertical/lateral polarization degree of the background part where light does not transmit through the transparent object 114A is displayed in bright gradation. On the other hand, the vertical/lateral polarization degree of the region where light transmitted through the transparent object 114A is slightly shifted to the dark gradation side because of the change in the polarization direction of the transmission light, the change being caused by birefringence. On the other hand, in the monochrome luminance image of FIG. 10A, only the edge portion of the transparent object 114A is slightly displayed in white. Therefore, in the image processing process, it appears to be difficult to distinguish the transparent object 114A from the placing table 113. As described above, when the vertical/lateral polarization degree image is used, the contrast between the region of the transparent object 114A and the rest of the region may become clear, namely it may become possible to explicitly distinguish the region of the transparent object 114A from the rest of the region. Because of this feature, it may become possible to extract the region of the transparent object 114A based on the following image processing procedure (flow).

As described above, by using the vertical/lateral polarization degree image, it may become possible to display a region in dark gradation or bright gradation, the region corresponding to the existence region of the transparent object 114A in an image made of acquired pixel values in the memory, so that the contrast between the region and the background region may become high (clear). Because of this feature, it may become possible to detect the position, the posture, the size and the like of the transparent object 114A.

Combination with Extraction of Region Using Luminance Image

Further, in addition to the extraction of the region by using the vertical/lateral polarization degree image, by extracting the region using the luminance image, it may become possible to further improve the detection accuracy. In this case, to improve the accuracy of extracting the region in the luminance image, for example, a light source may be disposed at a position between the placing table 113 and the polarization filter 112 and the light source may irradiate the polarization filter 112. Namely, in this disposition, the net (pattern) part of the placing table 113 is displayed as a shadow of light in dark gradation, which may make it easier to distinguish the region of the transparent object 114A from the net (pattern) part of the placing table 113.

Figure 11A:
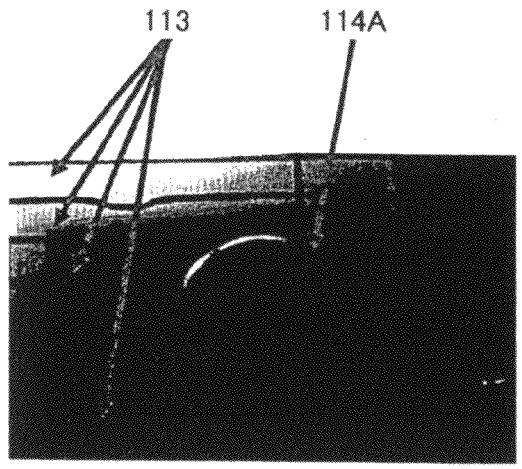
FIG. 11A is a drawing illustrating a monochrome luminance image of a third example of an acquired image of a transparent object.
Figure 11B:
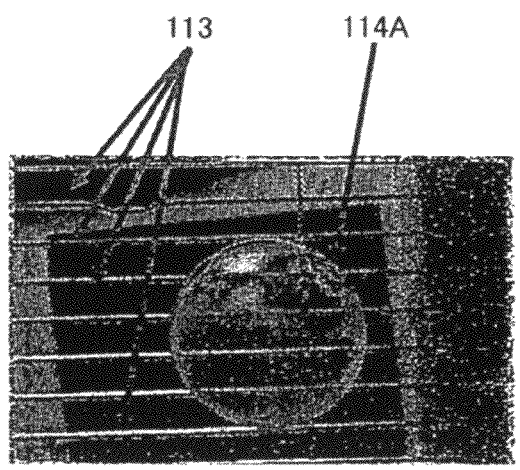
FIG. 11B is a drawing illustrating a vertical/lateral polarization degree image of the third example.

FIGS. 11A and 11B illustrate examples of the images acquired by the camera 12 in this case. FIG. 11A illustrates an example of the monochrome luminance image and FIG. 11B illustrates an example of the vertical/lateral polarization degree image.

As illustrated in FIG. 11B, the vertical/lateral polarization degree of the background part where light does not transmit through the transparent object 114A is displayed in dark gradation. On the other hand, the vertical/lateral polarization degree of the region where light transmitted through the transparent object 114A is slightly shifted to the bright gradation side because of the change in the polarization direction of the transmission light, the change being caused by birefringence. On the other hand, in the monochrome luminance image of FIG. 11A, unlike the image of FIG. 9A, the part of the placing table 113 and the edge portion of the transparent object 114A is emphasized.

Configuration without Polarization Filter

Further, the transparent object detection system 1A according to this embodiment of the present invention may not include the polarization filter 112. In this case, the transparent object detection system 1A includes the image acquisition unit (camera 12), the placing table 113, the tray 111, and an image processing apparatus 13. The image acquisition unit (camera 12) acquires images of the vertical polarization image and the horizontal polarization image by acquiring an image of the first region, the image including a transparent object 114A having characteristics in which a polarization direction of transmission light changes. The placing table 113 is provided so that the transparent object 114A is placed on the placing table 113. The placing table 113 reflects light having a polarization direction substantially the same as that of a third region, the third region being included in the first region, the image of the third region being acquired without including the transparent object 114A. The tray 111 is a base which is disposed opposite to the image acquisition unit (camera 12) across the placing table 113 and where a gradation value of one of the vertical polarization image and the horizontal polarization image is higher (stronger) than a gradation value of the other of the vertical polarization image and the horizontal polarization image. The image processing apparatus 13 detects the transparent object 114A based on the distributions of the vertical/lateral polarization degree of a vertical/lateral polarization degree image based on the vertical polarization image and the horizontal polarization image.

In such a transparent object detection system 1A having no polarization filter 112, the light from the lower side (base) of the placing table 113 has a specific strong polarization direction. To that end, for example, the tray 111 that causes the reflected light from the tray 111 to have a specific strong polarization direction may be used. In this case, it is preferable that the material of the tray 111 is the same as the material of the placing table 113.

Figure 12A:
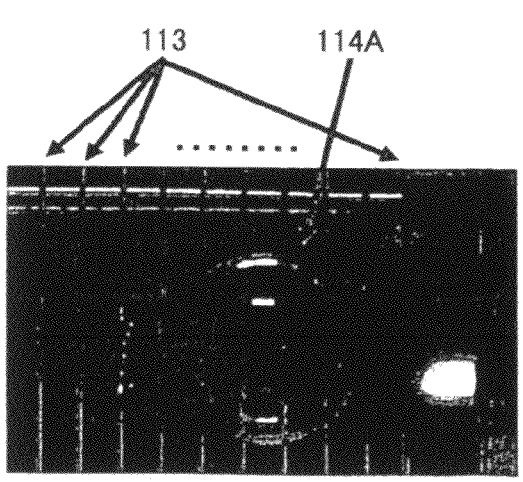
FIG. 12A is a drawing illustrating a monochrome luminance image of a fourth example of an acquired image of a transparent object.
Figure 12B:
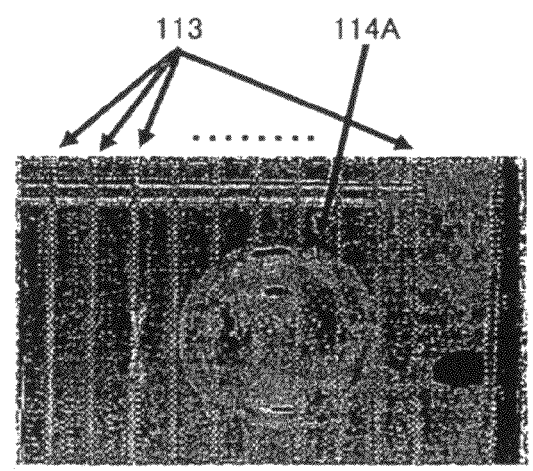
FIG. 12B is a drawing illustrating a vertical/lateral polarization degree image of the fourth example.

FIGS. 12A and 12B illustrate examples of the images acquired by the camera 12 in the case where the polarization filter 112 is not provided. FIG. 12A illustrates an example of the monochrome luminance image and FIG. 12B illustrates an example of the vertical/lateral polarization degree image.

As illustrated in FIG. 12B, when compared with the background light having slight dark gradation, the light transmitted through the transparent object 114A is slightly shifted to the bright gradation side. Therefore, even when the polarization filter 112 is not used, the contrast between the region of the transparent object 114A and the region other than the region of the transparent object 114A may become high (clear). By having the configuration in, which the transparent object 114A is not provided (used) as described above, the system may be simplified and the cost of the system may be reduced.

First Embodiment of Transparent Object Region Extraction Flow

Figure 13:
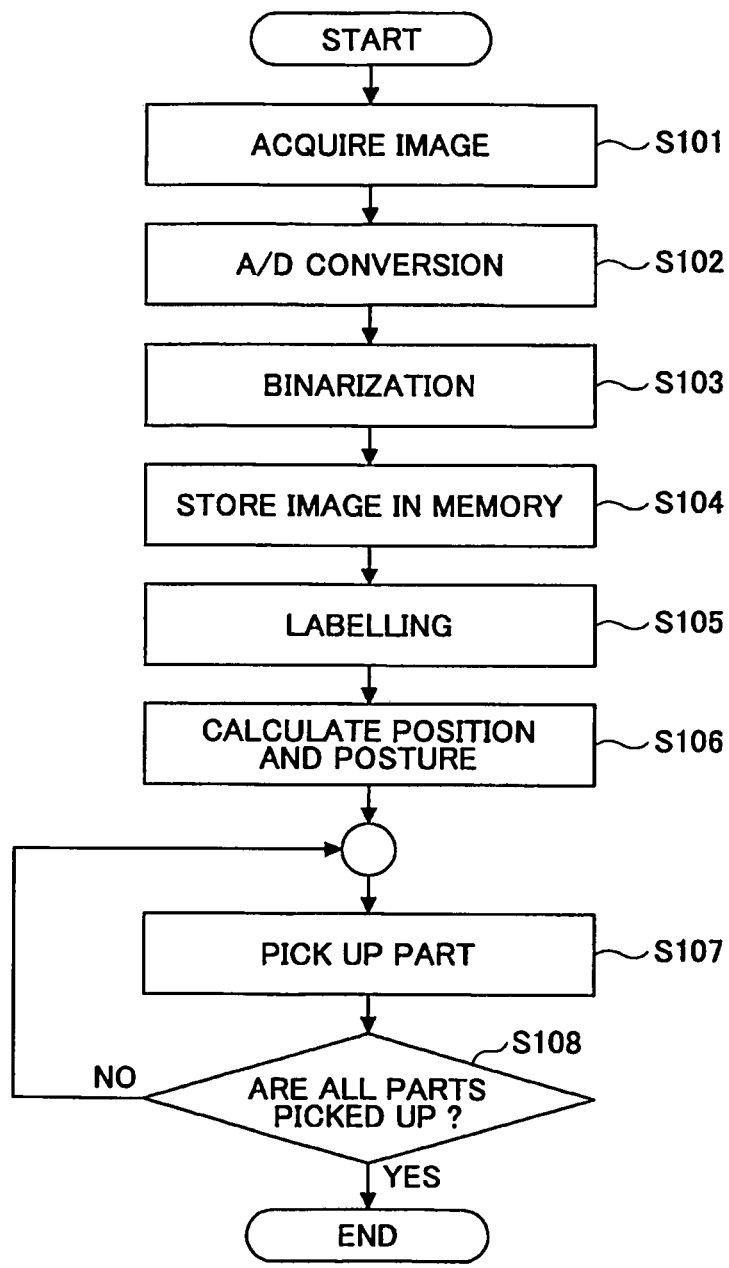
FIG. 13 is an example of a flowchart of an image processing process to be executed by an image processing apparatus.

FIG. 13 is a flowchart illustrating a processing flow executed by the image processing apparatus 13 of the transparent object detection system 1A when the polarization direction of the polarization filter denotes the P component as illustrated in FIG. 9.

First, the vertical/lateral polarization degree image is acquired by the camera 12 (step S101). Then, the vertical/lateral polarization degree signal of the pixels based on the acquired vertical/lateral polarization degree image is A/D converted into digital data by the A/D converter 131 (step S102).

Next, a binarization process is performed on the digital data (step S103), and the binarized pixel values of the pixels are stored in the memory 132 as image data (step S104).

Next, to distinguish the bright gradation parts, each lump of the bright gradation parts is labelled (labeling process) (step S105), and a lump of the bright gradation part having an area larger than a predetermined area is detected. Further, the gravity center and the secondary moment of the lump of the bright gradation part having an area larger than the predetermined area are calculated. Then, the CPU 135 performs processes so that the calculated gravity center of the lump of the bright gradation part is determined as the position of the transparent object 114A and the direction of the secondary moment is determined as the posture of the transparent object 114A (step S106).

As described above, first, by detecting a lump of the bright gradation part having an area larger than the predetermined area, it may become possible to detect the transparent object 114A in image processing. Further, by calculating the gravity center and the secondary moment of the detected lump of the bright gradation part having an area larger than the predetermined area, it may become possible to determine the position and the posture of the transparent object 114A.

After the above detecting process, the CPU 135 performs a process of transmitting a control signal to the robot controller 15, the control signal being obtained based on the data of the position and the posture of the transparent object 114A. As a result, by controlling and driving the robot controller 15, the transparent object 114A may be picked up by the robot hand 16 in accordance with the posture of the transparent object 114A and arranged and packed in a tray (not shown) (step S107). This packing process is repeated until all the detected transparent objects 114A are packed (steps S108 and S109).

Further, the calculation of vertical/lateral polarization degree in the above process is performed as follows. By using the camera 12, the vertical polarization component (P), the horizontal polarization component (S), raw polarization image data including the vertical polarization component (P) and the horizontal polarization component (S) are obtained. Based on the obtained vertical polarization component (which is also called "P polarization component" or "P component") and the horizontal polarization component (which is also called "S polarization component" or "S component"), a vertical/lateral polarization degree information Processing section generates the vertical/lateral polarization degree image and determines (calculates) the vertical/lateral polarization degree. In this calculation, the vertical/lateral polarization degree image data (vertical/horizontal polarization degree) are obtained by the following formula (1).

vertical/horizontal polarization degree=((*P* polarization component−*S* polarization component)/(*P* polarization component+*S* polarization component))      formula (1)

Further, to calculate (determine) the position and the posture, a template may be provided in advance and the position and the posture may be determined based on the template. The shape of the transparent object 114A is not limited to the spherical shape as illustrated in FIGS. 9A and 9B. For example, images rotated every one degree are provided in the template, and based on the template, the posture according to the rotating condition may be calculated.

Other imaging processes performed by the image processing apparatus 13, namely image processing such as a binarizing process, processes of calculating the gravity center and the secondary moment, are not limited to processes based on specific algorithms and may be performed based on respective known or new algorithms. Therefore, detailed descriptions thereof are herein omitted. Further, threshold values used in the processes may be appropriately set depending on the size, the shape and the like of the transparent object 114A.

As described above, in the transparent object detection system 1A according to this embodiment of the present invention, the contrast between the part where the transparent object 114A exists and the other part may become high (clear), thereby enabling detecting the transparent object 114A. Further, the vertical/lateral polarization degree image data are acquired. Therefore, without depending on the direction of the polarization filter 112 disposed under the transparent object 114A, it may become possible to detect the polarization change of the transparent object 114A, thereby enabling eliminating the calibration operation. Further, the rotation mechanism may not be necessary (Problem 3 may be resolved). Further, as the light to be transmitted to the transparent object 114A, the light having been transmitted through the polarization filter 112 is used. It is not necessary to dispose a lighting apparatus right below the polarization filter 112 (Problem 1 may be resolved). Further, in a configuration where the placing table 113 is disposed above the tray 111, the polarization filter 112 is disposed between the placing table 113 and the tray 111. It may not be necessary to perform an operation to relocate the transparent object 114A from the placing table 113 to a transparent object detection apparatus (Problem 2 may be resolved).

Further, it may become possible to easily and accurately calculate (determine) the position and the posture of the transparent object 114A detected by the image processing. Further, based on the calculated position and the posture of the transparent object 114A, it may become possible to accurately pick up the transparent object 114A by using the robot hand 16.

Defect Inspection

Further, in the transparent object detection system 1A, in addition to the detection of the position and the posture of the transparent object 114A, it is preferable to inspect whether there is a deficiency such as a missing portion, a burr and the like.

Figure 14:
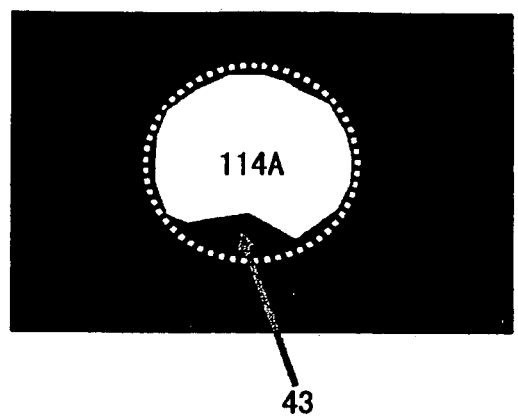
FIG. 14 is a drawing illustrating where a transparent object has a missing portion.
Figure 15:
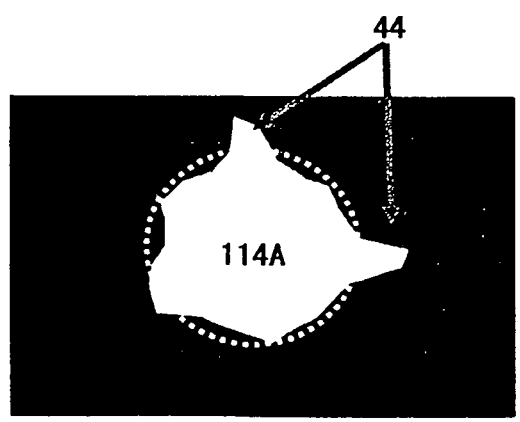
FIG. 15 is a drawing illustrating where a transparent object has burr.

To that end, first, similar to the above, the existence region of the transparent object 114A is specified. In this case, when there is a deficiency (fault) of a missing portion 43 in the transparent object 114A, as illustrated in FIG. 14, the size of the bright gradation part of the obtained (binarized) vertical/lateral polarization degree image becomes smaller than the existence region of a non-defective transparent object 114A. On the other hand, when the transparent object 114A has burrs 44 as illustrated in FIG. 15, the size of the bright gradation part of the obtained (binarized) vertical/lateral polarization degree image exceeds the existence region of the non-defective transparent object 114A.

In this case, the number of the pixels of the existence region of the non-defective transparent object 114A is known. Therefore, based on the number of the pixels, a normal range between an upper limit value and a lower limit value may be determined as a reference to be used for determining whether the transparent object 114A has a deficiency. Then, after the existence region of the transparent object 114A is specified, the number of the pixels of the bright gradation part of the transparent object 114A is counted. When the counted number is in the normal range, it may be determined that the transparent object 114A has no deficiency. When the counted number is greater than the upper limit value, it may be determined that the transparent object 114A has the deficiency of the burr 44. When the counted number is less than the lower limit value, it may be determined that the transparent object 114A has the deficiency of the missing portion 43. By doing in this way, the deficiency of the shape of the missing portion 43 and the burr 44 which may be caused in the transparent object 114A may be detected, thereby enabling determining whether the transparent object 114A is non-defective or defective.

Transparent Foreign Matter Inspection

Further, preferably, the transparent object detection system 1A is used for inspecting whether there is transparent foreign matter inside a translucent bottle. Namely, when there is transparent foreign matter, the transparent foreign matter is imaged as a lump of the bright gradation part or a lump of the dark gradation part in the vertical/lateral polarization degree image. Because of this feature, it may become possible to determine whether there is the transparent foreign matter depending on whether there is the lump in the image. Therefore, it may become possible to detect the transparent foreign matter remaining in an empty bottle or in a bottle filled with transparent fluid.

Second Embodiment of Transparent Object Region Extraction Flow

Another processing flow is described that is executed by the image processing apparatus 13 of the transparent object detection system 1A. In the processing flow in the second embodiment, unlike the processing flow in the first embodiment, not only the vertical/lateral polarization degree image but also the luminance image is used so as to detect deficiencies such as a stain, a scratch, and a crack and character information such as logos and marks, and image information, thereby enabling increasing the number of sortings when the transparent objects 114A are packed.

Next, the generation of the monochrome luminance information using the polarization information from the camera 12 is described. A monochrome luminance processing section generates a monochrome image and calculates luminance information using the acquired P component and S component. Further, the monochrome luminance is obtained by generating and outputting luminance information image data based on the following formula (2).

Monochrome luminance=$P$ polarization component+$S$ polarization component    formula (2)

When the inspection is performed for detecting whether there are deficiencies such as a stain, a scratch, and a crack caused on the transparent object 114A, the position and the posture of the transparent object 114A are obtained based on the processing flow in FIG. 13, and the existence region of the transparent object 114A is specified.

Figure 16:
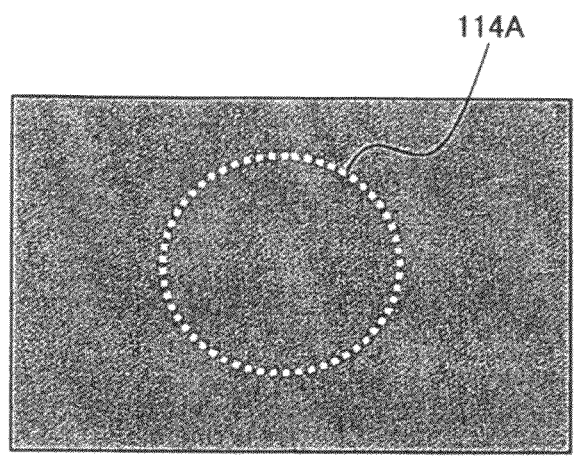
FIG. 16 is a drawing illustrating where a transparent object has no blemish.
Figure 17:
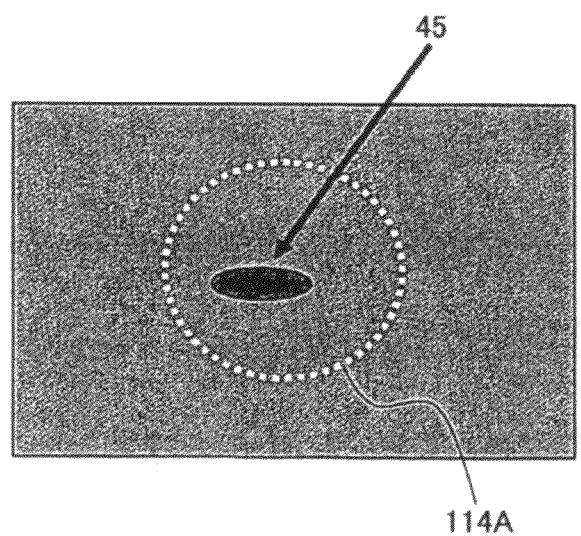
FIG. 17 is a drawing illustrating where a transparent object has blemish.

In this case, when there is no deficiency in the transparent object 114A, as illustrated in FIG. 16, a low contrast image is acquired in the existence region in the image acquired as the monochrome luminance image. On the other hand, when there is a deficiency (e.g., a stain 45) in the transparent object 114A, as illustrated in FIG. 17, the part corresponding to the stain 45 becomes darker than the surrounding part, and, partially, the contrast between the part corresponding to the stain 45 and the surrounding part becomes high (clear).

By using this feature, in the existence region of the transparent object 114A of the luminance image, it is determined whether the size or the changing level of the part where luminance distribution of the monochrome luminance image changes is within a normal range. Namely, the number of the pixels having brightness lower than a predetermined brightness is measured. Then, based on the measurement result, it may be determined whether there is the deficiency. For example, when determining that the number of the pixels in the measurement result is greater than a predetermined inspection threshold value, it may be determined that there is the deficiency. Otherwise, it may be determined that there is no deficiency. By doing in this way, it may become possible to detect surface deficiency such as the stain, the scratch, and the crack produced on the transparent object 114A, thereby enabling determining whether the transparent object 114A is non-defective or defective.

Further, after the position and the posture of the transparent object 114A are specified by using the vertical/lateral polarization degree image, it is preferable to detect the character information and design pattern information such as the logo and the mark formed (described) on the surface of the transparent object 114A based on the size or the changing level of the part where luminance distribution of the monochrome luminance image changes in the monochrome luminance image. By doing this, it may become possible to, for example, pick up the transparent object 114A based on the character information and the design pattern information as well as the determination of the shape.

Next, exemplary configurations of a transparent flat plate detection system are described based on embodiments of the present invention with reference to FIGS. 4 through 8 and FIGS. 18 through 30.

Transparent Flat Plate Detection System

First Embodiment

A transparent flat plate detection system 1B according to an embodiment of the present invention includes an image acquisition unit (camera 12), a placing table 113, a polarization filter 112, a reflection surface 115, a light shielding plate 102, and an image processing apparatus 13. The image acquisition unit (camera 12) acquires images of a vertical polarization image and a horizontal polarization image by acquiring an image of a region with a prescribed angle with respect to the normal direction of the flat surface part of a transparent flat plate 114B, the image including the transparent flat plate 114B. The placing table 113 is provided so that the transparent flat plate 114B is placed on the placing table 113. The reflection surface 115 is disposed on the optical path passing through the transparent flat plate 114B and the image acquisition unit (camera 12) and under the placing table 113. The light shielding plate 102 is disposed so as to face the image acquisition unit (camera 12) with respect to the normal line of the flat surface part of the transparent flat plate 114B and blocks light so as to prevent the mirror reflection light from the flat surface part of the transparent flat plate 114B from being incident on the image acquisition unit (camera 12). The image processing apparatus 13 detects the transparent flat plate 114B based on the distributions of vertical/lateral polarization degree of a vertical/lateral polarization degree image based on the vertical polarization image and the horizontal polarization image.

Figure 18:
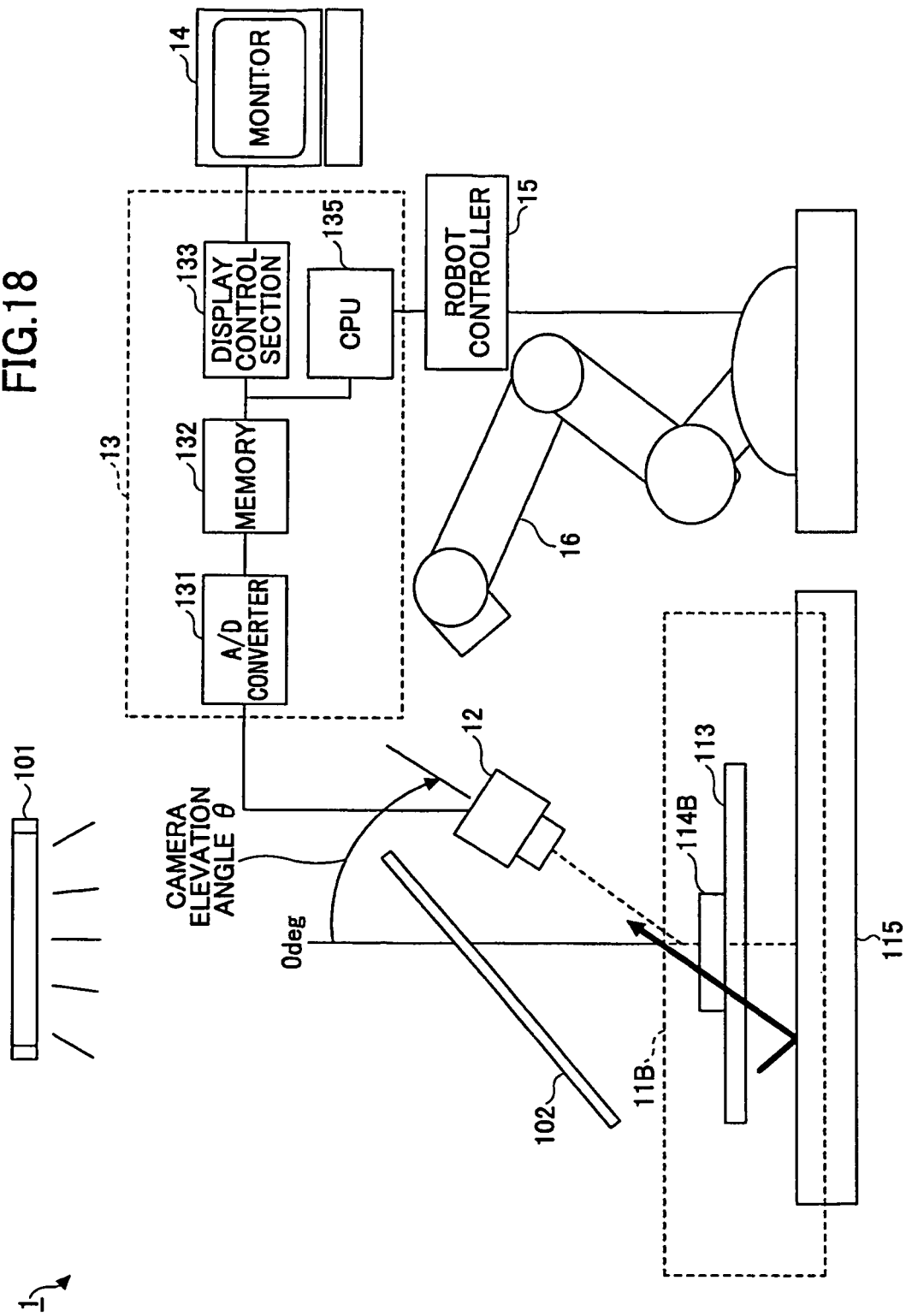
FIG. 18 is a drawing illustrating a transparent flat plate detection system according to an embodiment of the present invention.

FIG. 18 schematically illustrates a configuration of the transparent flat plate detection system 1B. The transparent flat plate detection system 1B includes a transparent flat plate placing section 11B, the camera 12, the image processing apparatus 13, the monitor 14, the robot controller 15, and the robot hand 16. The camera 12 acquires both a monochrome luminance image and a vertical/lateral polarization degree image.

For example, the transparent flat plate detection system 1B is installed in a manufacturing facility and disposed under indoor lighting such as a fluorescent light 101. Further, the transparent flat plate detection system 1B is disposed in a manner such that the placing table 113 of the transparent flat plate detection system 1B is parallel to the ground, and the camera 12 is disposed in a manner such that the image of the transparent flat plate 114B is acquired, with a predetermined elevation angle with respect to a normal direction of the placing table 113. Further, the light shielding plate 102 is disposed between the camera 12 and the indoor lighting (e.g., the fluorescent light 101) so that the indoor lighting cannot directly irradiate the transparent flat plate 114B. However, light from the overhead fluorescent light 101 may be shielded partially. As the light shielding plate 102, for example, a plastic plate on which black cloth is pasted may be used. However, any other plate or the like having sufficient light shielding capability may be alternatively used.

By disposing the light shielding plate 102, unnecessary reflection light on the surface of the transparent flat plate 114B may be avoided, and the camera 12 acquires an image of light incident upon and transmitted through the transparent flat plate 114B. As a result, it may become possible to detect the change of the polarization condition caused by the light transmission without being buried by the mirror reflection light. Therefore, it may become possible to improve the accuracy of detecting the transparent flat plate 114B.

The transparent flat plate placing section 11B includes the placing table 113 and the reflection surface 115. The placing table 113 is provided so that the transparent flat plate 114B is placed on the placing table 113. The reflection surface 115 is disposed opposite to the camera 12 across the placing table 113. As the reflection surface 115, for example, a tray may be used so as to receive droplets from the transparent flat plate 114B after, for example, a cleaning process of the transparent flat plate 114B.

Further, the placing table 113 has a net (mesh) structure in a manner such that a mesh (pattern) occupation rate of the net (mesh) structure is determined so that light reflected from the reflection surface 115 and then transmitted through the polarization filter 112 can be sufficiently transmitted through the transparent flat plate 114B. Specifically, it is preferable that the mesh (pattern) occupation rate is approximately 5% of the region of the transparent flat plate 114B. Further, it is preferable that the wires of the mesh (pattern) be thin, so that the width of each wire is equal to or less than 5% of the size of the transparent flat plate 114B. By having the size (structure) described above, the size of the region where polarized light transmits through the transparent flat plate 114B may be increased and the size of the background region may also be increased, thereby enabling improving the accuracy of detecting the edge of the transparent flat plate 114B.

The camera 12 used in this embodiment acquires an luminance monochrome image and a vertical/lateral polarization degree image as well. Pixel signals of two-dimensional acquired images are output (transmitted) from the respective sensors in the camera 12 to the image processing apparatus 13.

The image processing apparatus 13 includes an A/D converter 131, a memory 132, a display control section 133, a CPU 135, and a communication control section (not shown). The A/D converter 131 performs A/D conversion the pixel signals into digital binary values or multiple values. The memory 132 stores those values. The display control section 133 controls the display of the monitor 14. The communication control section performs communication control on a control signal for the robot-controller 15. The CPU 135 performs various image processing and calculations based on the programs stored in a ROM (not shown) or the like.

The image processing apparatus 13 detects the position, the posture, the size (existence region) and the like of the transparent flat plate 114B based on the images acquired by the camera 12 by using projected light distribution (bright-dark distribution) of the image data stored in the memory 132.

Further, in the image processing apparatus 13, the display control section 133 causes the monitor 14 to display the results of the obtained position, posture and the like of the transparent flat plate 114B. Further, in the image processing apparatus 13, a control signal obtained based on the position, the posture and the like of the transparent flat plate 114B are transmitted to the robot controller 15.

The monitor 14 is a display apparatus such as a LCD or a CRT. The robot controller 15 performs control to drive the robot hand 16 based on the control signals transmitted from the image processing apparatus 13. The robot hand 16 picks up the transparent flat plate 114B placed on the placing table 113 and arranges and stores the picked-up transparent flat plate 114B in a storage section (not shown) such as tray under the drive control from the robot controller 15.

Image Acquisition Unit

Next, a configuration of the camera 12 serving as an image acquisition unit that acquires the vertical/lateral polarization degree image is described. The camera 12 acquires an image of a surrounding area including the transparent flat plate 114B, the image having a megapixel size or the like, by using an imaging acquisition device (light receiving device) such as a CCD (Charge-Coupled Device) or a CMOS (Complementary Metal Oxide Semiconductor). The camera 12 used in the transparent flat plate detection system 1B according to this embodiment of the present invention acquires not only a luminance image but also a polarization image. In the following, the camera 12 for acquiring (forming) the polarization image is described.

First Embodiment of Image Acquisition Unit (Camera)

In this embodiment, as schematically illustrated in FIG. 4, the camera 12 includes a first camera and a second camera, the first camera being for acquiring a vertical polarization image using a polarization filter 20a disposed at a position where a polarization light polarized in the vertical direction transmits, the second camera being for acquiring a lateral polarization image using a polarization filter 20b disposed at a position where a polarization light polarized in the lateral direction transmits. By having this structure, the camera 12 may acquire both the vertical polarization image and the lateral polarization image at the same time unlike a conventional camera that does not acquire those images at the same time and without rotating the polarization filters which may cause time delay between the acquired images.

Further, unlike a known stereo method, first and second cameras may be disposed close to each other. Recently, there has been a strong demand for reducing the size of the apparatus. As a structure further reducing the size of the camera in FIG. 4, it is preferable that, as illustrated in FIG. 5, the camera 12 has a structure acquiring the images using a single light receiving device via the lens array and the polarizer filter array.

FIG. 5 schematically illustrates a configuration of an optical system 21 of the camera 12. The optical system 21 includes two optical systems, one optical system being for acquiring the vertical polarization image, the other optical system being for acquiring the lateral polarization image. Further, a lens array 22, a light shielding spacer 23, a polarization filter 24, a spacer 25, and a solid-state image acquisition unit 26 are formed and laminated to each other.

The lens array 22 includes two lenses 28a and 28b. Each of the two lenses 28a and 28b is made of a single lens having the same shape such as a hemisphere lens and the like. The two lenses 28a and 28b have the respective optical axes 27a and 27b parallel to each other. Further, the two lenses 28a and 28b are disposed on the same plane. Namely, when the direction parallel to each of the optical axes 27a and 27b is defined as Z direction, one direction perpendicular to the Z direction is defined as the X direction, and the direction perpendicular to the Z direction and the X direction is defined as the Y direction, the two lenses 28a and 28b are disposed on the same XY plane.

The light shielding spacer 23 has two apertures 29a and 29b, and is disposed opposite to an object-of-shooting side (side where an object to be imaged is disposed) with respect to the lens array 22. The apertures 29a and 29b are through holes having a predetermined size and having centers disposed on the respective optical axes 27a and 27b. Further, an optical anti-reflective treatment is performed on the inner walls of the apertures 29a and 29b, the optical anti-reflective treatment including black coating, rough surface, matte finish or the like.

The polarization filter 24 includes two polarizer regions 30a and 30b having the respective polarization planes being different by 90 degrees from each other. The polarization filter 24 is disposed opposite to the lens array 22 with respect to the light shielding spacer 23. The polarizer regions 30a and 30b are disposed in a manner such that the centers of the polarizer regions 30a and 30b are disposed on the optical axes 27a and 27b, respectively, and further disposed on an XY plane. Each of the polarizer regions 30a and 30b is provided for polarizing unpolarized light in which the electric field and the magnetic field are vibrated in unspecific directions so as to transmit only a linearly-polarized light having a vibration component along the specified polarization plane direction.

The spacer 25 has a rectangular frame shape having an aperture 31 which is a through hole including a region corresponding to the polarizer regions 30a and 30b of the polarization filter 24. The spacer 25 is disposed opposite to the light shielding spacer 23 with respect to the polarization filter 24.

The solid-state image acquisition unit 26 includes two solid-state image acquisition devices 33a and 33b mounted on a substrate 32 having a signal processing section (not shown). The solid-state image acquisition unit 26 is disposed opposite to the polarization filter 24 with respect to the spacer 25. Imaging regions of the solid-state image acquisition devices 33a and 33b are disposed in a manner such that the centers of the imaging regions of the solid-state image acquisition devices 33a and 33b are disposed on the optical axes 27a and 27b, respectively, and are disposed on an XY plane. The imaging regions are regions where images of an object to be imaged are formed. When each of the solid-state image acquisition devices 33a and 33b senses (acquires) a black and white image, no color filter is included. On the other hand, when each of the solid-state image acquisition devices 33a and 33b senses (acquires) a color image, a color filter is disposed at a previous stage.

Second Embodiment of Image Acquisition Unit (Camera)

In this embodiment, as schematically illustrated in FIG. 6, it is preferable to use a camera 12 in which a single imaging lens (or plural lenses in the same axis) is used to acquire (form) an image, and at a subsequent stage, an image is divided into the vertical polarization image and the lateral (horizontal) polarization image to form the vertical/lateral polarization degree image.

To acquire the vertical polarization image and the lateral polarization image, as schematically illustrated in FIG. 6, the camera 12 includes a half mirror box 34, a mirror 35, a vertical polarization filter 36, a horizontal polarization filter 37, and CCDs 38 and 39. The half mirror box 34 has transmissivity of 1:1 (i.e., 50% of light is transmitted and 50% of the light is reflected). The CCDs 38 and 39 are provided for acquiring visual field images through the vertical polarization filter 36 and the horizontal polarization filter 37, respectively. The camera 12 in the first embodiment can acquire both the vertical polarization image and the lateral polarization image but parallax may occur between the acquired images. On the other hand, the camera 12 in the second embodiment does not cause parallax because the same imaging optical system (lens) is used for acquiring the images. Because of this feature, a detection region may become smaller and it may become no longer necessary to calibrate the parallax and the like.

Instead of using the half mirror box 34, a polarization beam splitter reflecting lateral polarization light and transmitting vertical polarization light may be used. When the polarization beam splitter is used, it becomes no longer necessary to have the vertical polarization filter 36 and the horizontal polarization filter 37. Further, it may become possible to simplify the configuration of the optical system and improve the light-use efficiency.

Third Embodiment of Image Acquisition Unit (Camera)

In this embodiment, as schematically illustrated in FIG. 7, it is preferable to use a camera 12 in which a single imaging lens (or plural lenses in the same axis) is used to acquired (form) an image, and at a subsequent stage of the lens, there is disposed a region-dividing-type polarization filter 24 including one or more polarizer regions transmitting only vertical polarization light and one or more polarizer regions transmitting only horizontal (lateral) polarization light. In this case, to form the polarizer regions, a region-dividing-type polarization filter 24 having the explicit boundaries between the regions may be formed by using the wiregrid method based on a metal having a fine concavo-convex shape or the autocloning-type photonic crystal method.

When the camera 12 in the second embodiment is used, the vertical polarization light and the lateral polarization light are obtained by separating light using a prism. Because of this feature, the size of the optical system may become larger, and two light receiving devices are required. On the other hand, when the camera 12 in the third embodiment is used, both the lateral polarization image and the vertical polarization image are acquired by the optical system having the same axis of the imaging lens.

In this embodiment, a configuration of the region-dividing-type polarization filter 24 is not limited to a configuration in which there is one-to-one correspondence between each pixel of the light receiving device and the corresponding filter. For example, it is preferable that the region-dividing-type polarization filter 24 may have the configuration as schematically illustrated in FIG. 8. In the configuration of FIG. 8, each square arranged in both vertical and lateral directions denotes a light receiving part of the respective light receiving devices (i.e., a light receiving device array 40). Two types of tilted bands denote the polarization filter regions in vertical and lateral directions 41 and 42. Each of the polarization filter regions 41 and 42 has a band shape. The width of the band shape corresponds to one pixel that is same as the width of one light receiving device. Further, a tilt value of the boundaries between the polarization filter regions 41 and 42 of the band shape is two (2), namely the angle of the tilt is determined by a one-pixel width in the lateral direction and a two-pixel length in the vertical direction (when it proceeds one pixel in the lateral direction, it also proceeds two pixels in the vertical direction).

By using such a specific disposal pattern of the filters and the signal processing techniques, it may become possible to re-create filter transmission images across the entire screen even when the accuracy of alignment when the imaging device array and the region-dividing-type polarization filters are joined is not sufficient, and it may become possible to realize such an image acquisition apparatus at low cost.

As described above, the camera 12 in the transparent flat plate detection system 1B according to this embodiment of the present invention acquires a polarization image. Further, preferably, an image of the transparent flat plate 114B can be acquired in real time, and the acquired image is supplied to the image processing apparatus 13.

Detection of Transparent Flat Plate

The camera 12 in the transparent flat plate detection system 1B according to this embodiment of the present invention particularly uses (detects) the change of the polarization condition of light obliquely transmitted through the transparent flat plate 114B. In the light incident on the parallel flat plates, the transmissivity of the vertical component (P component) differs from the transmissivity of the horizontal component (S component).

Figure 19:
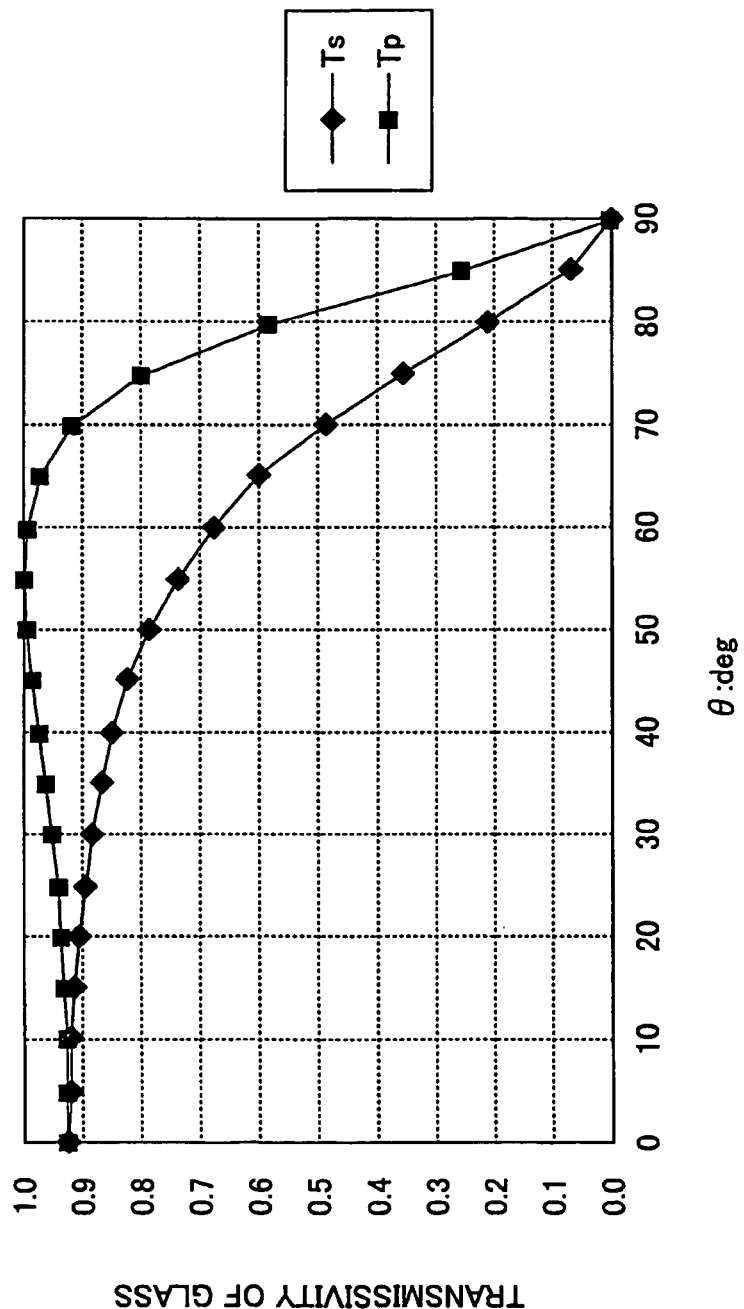
FIG. 19 is a graph illustrating an example of transmissivity of a transparent flat plate.

FIG. 19 illustrates the characteristics of the transmissivity of the light incident on a glass flat plate having a refractive index of 1.5 with an incident angle of θ. Specifically, as illustrated in FIG. 19, the transmissivity of the horizontal component (S component) simply decreases. However the transmissivity of the vertical component (P component) increases first and then decreases.

The transparent flat plate detection system 1B uses the change (difference) between the transmissivity of the horizontal component (S component) and the transmissivity of the vertical component (P component). In this case, as illustrated in FIG. 19, when the elevation angle is approximately 70 degrees, the difference between the P component and the S component is large and the transmissivity of the vertical component (P component) is sufficiently high (90% or more). Therefore, it is preferable to set the elevation angle in a range between, for example, 50 degrees and 70 degrees.

As described above, the camera 12 acquires the vertical/lateral polarization degree image. For example, the vertical/lateral polarization degree image has gradations (gradation values) (e.g., 256 gradations) in the polarization direction from horizontal component (S component) to vertical component (P component). In this case, for example, when light having the P component is incident, dark gradation is displayed. On the other hand, when light having the S component is incident, bright gradation is displayed.

FIGS. 20A and 20B illustrate examples of the images acquired by the camera 12. FIG. 20A illustrates an example of the monochrome luminance image, and FIG. 20B illustrates an example of the vertical/lateral polarization degree image.

As illustrated in FIG. 20B, the vertical/lateral polarization degree of the background part where light does not transmit through the transparent flat plate 114B is displayed in bright gradation. On the other hand, the vertical/lateral polarization degree of the region where light has transmitted through the transparent flat plate 114B is shifted to the dark gradation side. This is because the S component is reflected to the lower side of the transparent flat plate 114B and is decreased (attenuated), but the P component transmits without being reflected and as a result the light of P component is emphasized. On the other hand, in the monochrome luminance image of FIG. 20A, only the edge portion of the transparent flat plate 114B is slightly displayed in white. Further, in the image processing, it appears to be difficult to distinguish the transparent flat plate 114B from the placing table 113.

As described above, when the vertical/lateral polarization degree image is used, the contrast between the region of the transparent flat plate 114B and the rest of the region may become clear, namely it may become possible to explicitly distinguish the region of the transparent flat plate 114B from the rest of the region. Because of this feature, it may become possible to extract the region of the transparent flat plate 114B based on the following image processing procedure (flow).

First Embodiment of Transparent Flat Plate Region Extraction Flow

Figure 21:
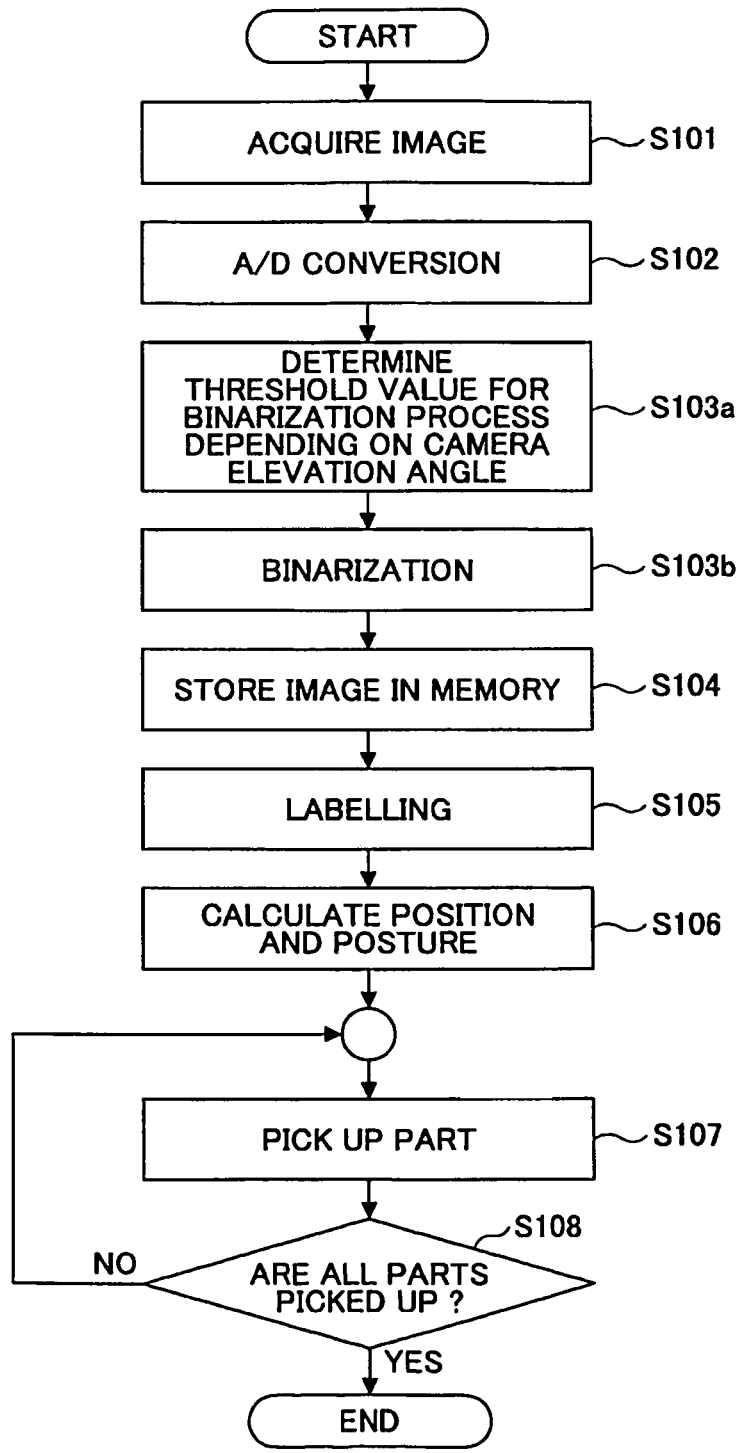
FIG. 21 is an exemplary flowchart of image processing performed by an image forming apparatus.

FIG. 21 is a flowchart illustrating a processing flow executed by the image processing apparatus 13 of the transparent flat plate detection system 1B when the light transmitted through the transparent flat plate is detected as illustrated in FIGS. 20A and 20B.

First, the vertical/lateral polarization degree image is acquired by the camera 12 (step S101). Then, each vertical/lateral polarization degree signal of the pixels based on the acquired vertical/lateral polarization degree image is A/D converted into digital data by the A/D converter 131 (step S102).

Next, a threshold value to be used in the binarization process is set in accordance with the camera elevation angle (step S103a), and the binarization process is performed on the digital data (step S103b). Then, the binarized pixel values of the pixels are stored in the memory 132 as image data (step S104).

Figure 22:
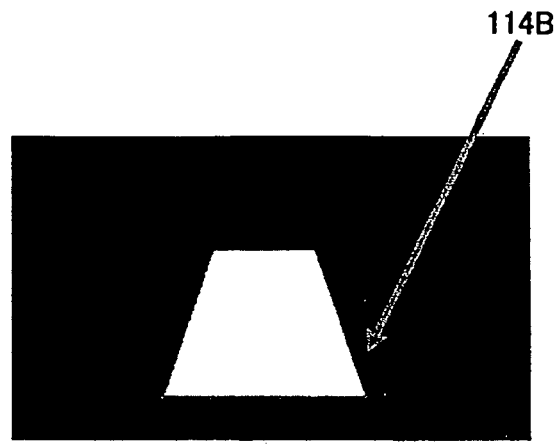
FIG. 22 is a drawing illustrating an example of an image obtained as a region extraction result of a transparent flat plate.

Next, to distinguish the dark gradation parts from each other, each lump of the bright gradation part (FIG. 22 illustrates an example of the extraction result) is labelled (labeling process) (step S105), and a lump of the bright gradation part having an area larger than a predetermined area is detected. Further, the gravity center and the secondary moment of the lump of the bright gradation part having an area larger than the predetermined area are calculated. Then, the CPU 135 performs processes where the calculated gravity center of the lumps of the bright gradation part is determined as the position of the transparent flat plate 114B and where the direction of the secondary moment is determined as the posture of the transparent flat plate 114B (step S106).

As described above, first, by detecting a lump of the bright gradation part having an area larger than the predetermined area, it may become possible to detect the transparent flat plate 114B in image processing. Further, by calculating the gravity center and the secondary moment of the detected lump of the bright gradation part having an area larger than the predetermined area, it may become possible to determine the position and the posture of the transparent flat plate 114B.

After the above detecting process, the CPU 135 performs a process of transmitting a control signal to the robot controller 15, the control signal being obtained based on the data of the position and the posture of the transparent flat plate 114B. As a result, by controlling and driving the robot controller 15, the transparent flat plate 114B may be picked up by the robot hand 16 in accordance with the posture of the transparent flat plate 114B and arranged and packed in a tray (not shown) (step S107). This packing process is repeated until all the detected transparent flat plates 114B are packed (steps S108 and S109).

Further, the calculation of vertical/lateral polarization degree in the above process is performed as follows. By using the camera 12, the vertical polarization component (P), the horizontal polarization component (S), raw polarization image data including the vertical polarization component (P) and the horizontal polarization component (S) are obtained. Based on the obtained vertical polarization component (which is also called "P polarization component" or "P component") and the horizontal polarization component (which is also called "S polarization component" or "S component"), the vertical/lateral polarization degree image is generated and the vertical/lateral polarization degree is determined (calculated). In this calculation, the vertical/lateral polarization degree image data (vertical/horizontal polarization degree) are obtained by the following formula (3).

vertical/horizontal polarization degree=((*P* polarization component−*S* polarization component)/(*P* polarization component+*S* polarization component))    formula (3)

Figure 23:
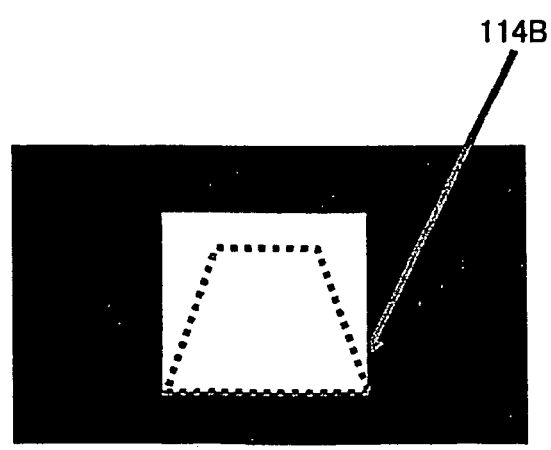
FIG. 23 is a drawing illustrating an image after trapezoidal distortion correction is performed.

Further, in a case where the transparent flat plate 114B is to be picked up, if the obtained image is inclined (e.g., the shape of the image is trapezoidal), it may be difficult to determine the center position and the like. In such a case, for example, it is preferable to perform a trapezoidal distortion correction process such as the affine transformation. By doing this, the image as illustrated in FIG. 22 may be converted into an image viewed from directly above as illustrated in FIG. 23, and as a result, it may become possible to improve the accuracy of extracting the position of the gravity center.

Further, to calculate (determine) the position and the posture, a template may be provided in advance and the position and the posture may be determined based on the template. The shape of the transparent flat plate 114B is not limited to the spherical shape as illustrated in FIGS. 20A and 20B, For example, images rotated every one degree are provided in the template, and based on the template, the posture according to the rotating condition may be calculated.

Other imaging processes performed by the image processing apparatus 13, namely image processing such as binarizing process, processes of calculating the gravity center and the secondary moment, are not limited to processes based on specific algorithms and may be performed based on respective known or new algorithms. Therefore, detailed descriptions thereof are herein omitted. Further, threshold values used in the processes may be appropriately set depending on the camera elevation angle θ and the size, the shape and the like of the transparent flat plate 114B.

As described above, in the transparent flat plate detection system 1B according to this embodiment of the present invention, the change of the polarization condition of the transmission light obliquely incident on the transparent flat plate 114B from the transparent flat plate 114B is used and unnecessary light of the mirror reflection light is blocked. Therefore, the contrast between the part where the transparent flat plate 114B exists and the other part may become high (clear), thereby enabling detecting the transparent flat plate 114B. Further, the vertical/lateral polarization degree image data are acquired. Therefore, without depending on the direction of the polarization filter 112 disposed under the transparent flat plate 114B, it may become possible to detect the polarization change of the transparent flat plate 114B, thereby enabling eliminating the calibration operation. Further, the rotation mechanism may not become necessary (Problem 3 may be resolved). Further, the mirror reflection light from the transparent flat plate 114B is not incident on the image acquisition unit (camera 12) and the light transmitted through the transparent flat plate 114B is used. Therefore, it is not necessary to provide a dedicated lighting apparatus, and even under the fluorescent light 101, it may become possible to detect the transparent flat plate 114B (Problem 1 may be resolved). Further, in a state where the placing table 113 is disposed above the tray and the transparent flat plate 114B is placed on the placing table 113 or in a state where the transparent flat plate 114B is placed directly on the placing table 113, it may become possible to detect the transparent flat plate 114B (Problem 2 may be resolved).

Further, it may become possible to easily and accurately calculate (determine) the position and the posture of the transparent flat plate 114B detected by the image processing. Further, based on the calculated position and the posture of the transparent flat plate 114B, it may become possible to accurately pick up the transparent flat plate 114B by using the robot hand 16.

Defect Inspection

Further, in the transparent flat plate detection system 1B, in addition to the detection of the position and the posture of the transparent flat plate 114B, it is preferable to inspect whether there is a deficiency such as a missing portion, a burr and the like.

Figure 24:
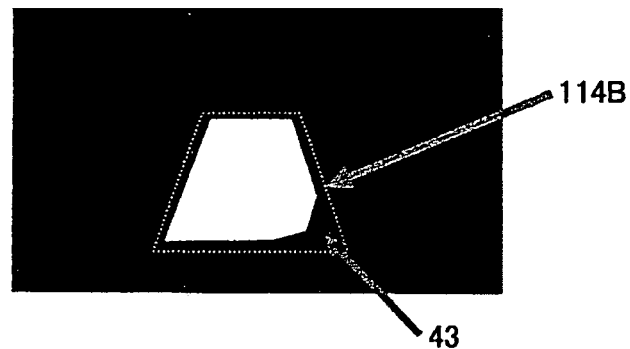
FIG. 24 is a drawing illustrating an exemplary image of a transparent flat plate having a missing portion.
Figure 25:
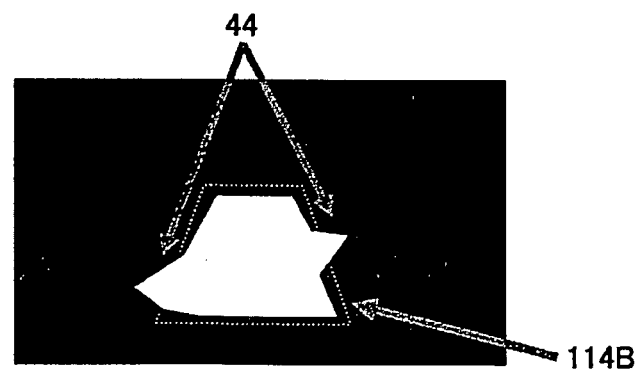
FIG. 25 is a drawing illustrating an exemplary image of a transparent flat plate having burrs.

To that end, first, similar to the above, the existence region of the transparent flat plate 114B is specified. In this case, when there is a deficiency (default) of a missing portion 43 in the transparent flat plate 114B, as illustrated in FIG. 24, the size of the bright gradation part of the obtained (binarized) vertical/lateral polarization degree image becomes smaller than the existence region of a non-defective transparent flat plate 114B. On the other hand, when the transparent flat plate 114B has burrs 44 as illustrated in FIG. 25, the size of the bright gradation part of the obtained (binarized) vertical/lateral polarization degree image exceeds the existence region of the non-defective transparent flat plate 114B.

In this case, the number of the pixels of the existence region of the non-defective transparent flat plate 114B is known. Therefore, based on the number of the pixels, a normal range between an upper limit value and a lower limit value may be determined as a reference to be used for determining whether the transparent flat plate 114B has a deficiency. Then, after the existence region of the transparent flat plate 114B is specified, the number of the pixels of the bright gradation part of the transparent flat plate 114B is counted. When the counted number is in the normal range; it may be determined that the transparent flat plate 114B has no deficiency. When the counted number is greater than the upper limit value, it may be determined that the transparent flat plate 114B has the deficiency of the burr 44. When the counted number is less than the lower limit value, it may be determined that the transparent flat plate 114B has the deficiency of the missing portion 43. By doing in this way, the deficiency of the shape of the missing portion 43 and the burr 44 which may be caused in the transparent flat plate 114B may be detected, thereby enabling determining whether the transparent flat plate 114B is non-defective or defective.

Transparent Foreign Matter Inspection

Further, preferably, the transparent flat plate detection system 1B is used for inspecting whether there is transparent foreign matter inside a translucent bottle. Namely, when there is transparent foreign matter, the transparent foreign matter is imaged as a lump of the bright gradation part or a lump of the dark gradation part in the vertical/lateral polarization degree image. Because of this feature, it may become possible to determine whether there is the transparent foreign matter depending on whether there is the lump in the image. Therefore, it may become possible to detect the transparent foreign matter remaining in an empty bottle or in a bottle which is filled with transparent fluid.

Second Embodiment of Transparent Flat Plate Region Extraction Flow

Another processing flow is described that is executed by the image processing apparatus 13 of the transparent flat plate detection system 1B. In the processing flow in the second embodiment, unlike the processing flow in the first embodiment, not only the vertical/lateral polarization degree image but also the luminance image is used so as to detect deficiencies such as a stain, a scratch, and a crack and character information such as logos and marks, and image information, thereby enabling increasing the number of sortings when the transparent flat plates 114B are packed.

Next, the generation of the monochrome luminance information using the polarization information from the camera 12 is described. A monochrome luminance processing section generates a monochrome image and calculates luminance information using the acquired P component and S component. Further, the monochrome luminance is obtained by generating and outputting luminance information image data based on the following formula (4).

Monochrome luminance=$P$ polarization component+$S$ polarization component     formula (4)

When the inspection is performed for detecting whether there are deficiencies such as a stain, a scratch, and a crack caused on the transparent flat plate 114B, the position and the posture of the transparent flat plate 114B are obtained based on the processing flow in FIG. 21, and the existence region of the transparent flat plate 114B is specified.

Figure 26:
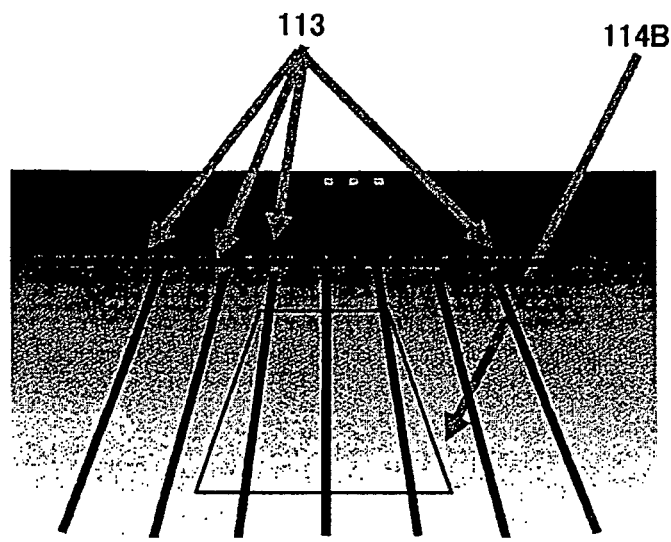
FIG. 26 is a drawing illustrating an exemplary image of a transparent flat plate without stain.
Figure 27:
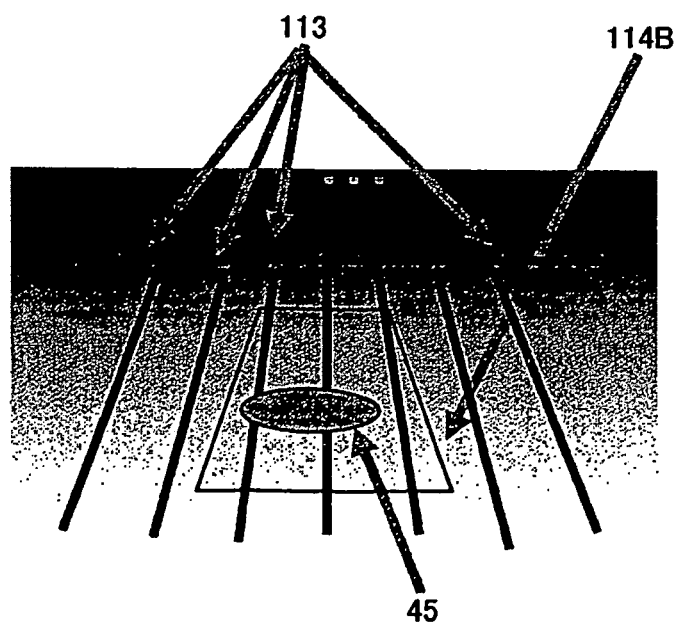
FIG. 27 is a drawing illustrating an exemplary image of a transparent flat plate with stain.

In this case, when there is no deficiency in the transparent flat plate 114B, as illustrated in FIG. 26, a low contrast image is acquired in the existence region in the image acquired as the monochrome luminance image. On the other hand, when there is a deficiency (e.g., a stain 45) in the transparent flat plate 114B, as illustrated in FIG. 27, the part corresponding to the stain 45 becomes darker than the surrounding part, and, partially, the contrast between the part corresponding to the stain 45 and the surrounding part becomes high (clear).

By using this feature, in the existence region of the transparent flat plate 114B of the luminance image, it is determined whether the size or the changing level of the part where luminance distribution of the monochrome luminance image changes is within a normal range. Namely, the number of the pixels having brightness lower than a predetermined brightness is measured. Then, based on the measurement result, it may be determined whether there is the deficiency. For example, when determining that the number of the pixels in the measurement result is greater than a predetermined inspection threshold value, it may be determined that there is the deficiency. Otherwise, it may be determined that there is no deficiency. By doing in this way, it may become possible to detect a surface deficiency such as the stain, the scratch, and the crack produced on the transparent flat plate 114B, thereby enabling determining whether the transparent flat plate 114B is non-defective or defective.

Further, after the position and the posture of the transparent flat plate 114B are specified by using the vertical/lateral polarization degree image, it is preferable to detect the character information and design pattern information such as the logo and the mark formed (described) on the surface of the transparent flat plate 114B based on the size or the changing level of the part where luminance distribution of the monochrome luminance image changes in the monochrome luminance image. By doing this, it may become possible to, for example, pick up the transparent flat plate 114B based on the character information and the design pattern information as well as the determination of the shape.

Transparent Flat Plate Detection System

Second Embodiment

A transparent flat plate detection system 1B according to another embodiment of the present invention is described.

The transparent flat plate detection system 1B according to this embodiment of the present invention includes an image acquisition unit (camera 12), a reflection plate 103, and an image processing apparatus 13. The image acquisition unit (camera 12) acquires images of a vertical polarization image and a horizontal polarization image by acquiring an image of a region with a prescribed angle with respect to the normal direction of the flat surface part of the transparent flat plate 114B, the image including the transparent flat plate 114B. The reflection plate 103 is disposed opposite to the image acquisition unit (camera 12) with respect to the normal line of the flat surface part of the transparent flat plate 114B and with an elevation angle so that the mirror reflection light from the transparent flat plate 114B is incident on the image acquisition unit (camera 12). The image processing apparatus 13 detects the transparent flat plate 114B based on the distributions of the vertical/lateral polarization degree of the vertical/lateral polarization degree image based on the vertical polarization image and the horizontal polarization image.

Figure 28:
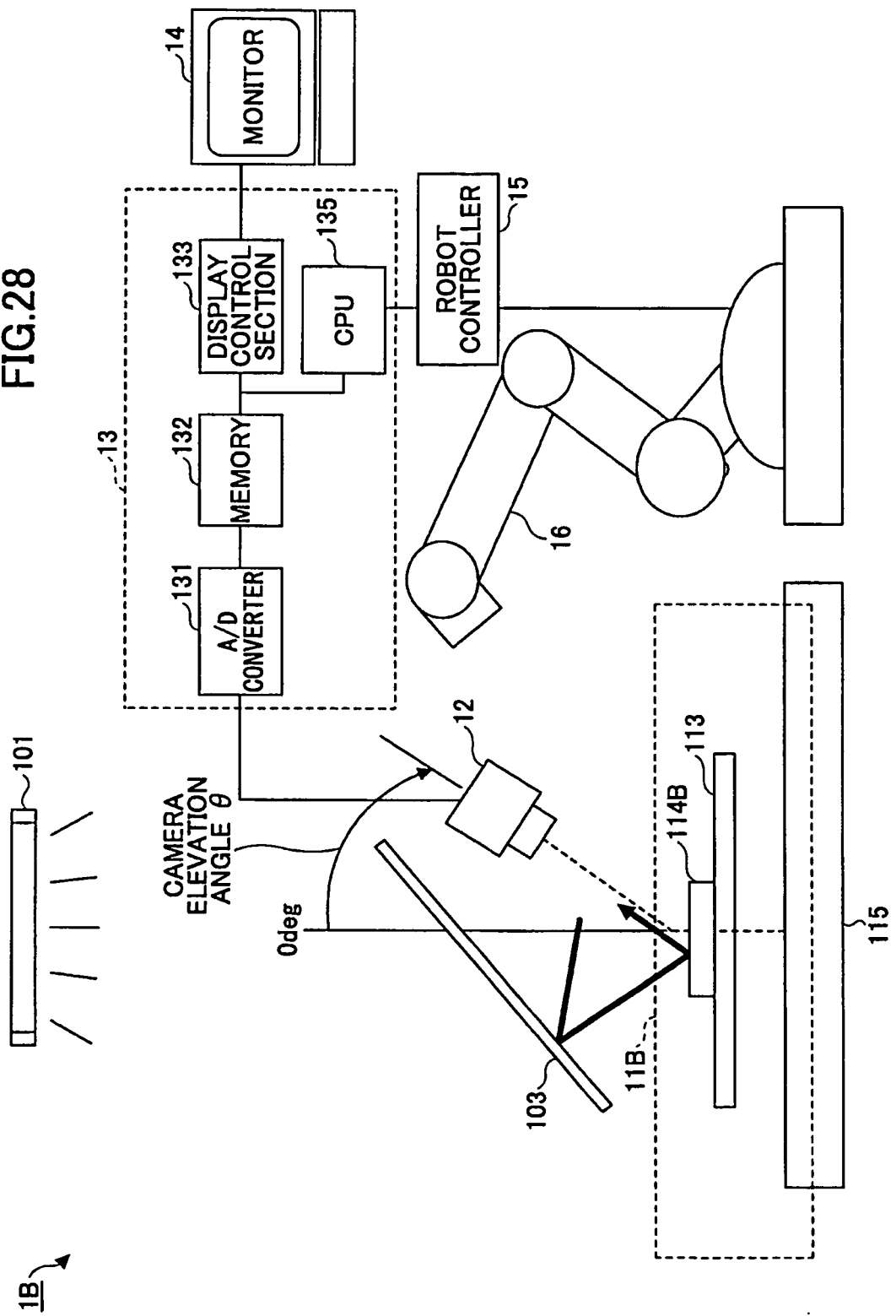
FIG. 28 is a drawing illustrating a transparent flat plate detection system according to another embodiment of the present invention.

FIG. 28 schematically illustrates a configuration of the transparent flat plate detection system 1B. The transparent flat plate detection system 1B includes a transparent flat plate placing section 11B, the camera 12, the image processing apparatus 13, the monitor 14, the robot controller 15, and the robot hand 16. The camera 12 acquires both a monochrome luminance image and a vertical/lateral polarization degree image. The transparent flat plate detection system 1B according to the second embodiment of the present invention includes the reflection plate 103 in place of the light shielding plate 102. The descriptions of the elements similar to those of the first embodiment are accordingly omitted.

For example, the transparent flat plate detection system 1B is installed in a manufacturing facility and disposed under indoor lighting such as a fluorescent light 101. Further, the transparent flat plate detection system 1B is disposed in a manner such that the placing table 113 of the transparent flat plate detection system 1B is parallel to the ground, and the camera 12 is disposed in a manner such that the image of the transparent flat plate 114B is acquired with a predetermined elevation angle with respect to normal direction of the placing table 113. Further, the reflection plate 103 is disposed so that while the indoor lighting does not directly irradiate the transparent flat plate 114B, not the light directly from the fluorescent light 101 but the light from the surroundings is incident on the transparent flat plate 114B and the reflected light of the light from the surroundings is incident on the camera 12. However, the light from the overhead fluorescent light 101 may be shielded partially. As the reflection plate 103, for example, a plastic plate may be used.

By disposing the reflection plate 103, unnecessary reflection light as the direct reflection light from the fluorescent light 101 may be removed, and the camera 12 acquires an image of the light incident upon and transmitted through the transparent flat plate 114B from the reflection plate 103. As a result, it may become possible to detect the change of the polarization condition caused upon the reflection without being disturbed by disturbance light such as light from the fluorescent light 101. Therefore, it may become possible to improve the accuracy of detecting the transparent flat plate 114B.

As in this embodiment of the present invention, when the transparent flat plate reflection light is used, the condition under the transparent flat plate 114B is not limited to a specific condition. However, it is preferable that a material having characteristics in which the P component is specifically reflected is used. A material especially reflecting the P component includes a material having internal scattering characteristics such as plastic. Therefore, for example, when a plastic tray is disposed under the transparent flat plate 114B, the contrast between the region of the transparent flat plate 114B and the region other than the region of the transparent flat plate 114B may become high (clear).

Detection of Transparent Flat Plate

The camera 12 in the transparent flat plate detection system 1B according to this embodiment of the present invention particularly uses (detects) the change of the polarization condition of light obliquely incident on and reflected by the transparent flat plate 114B. In the light incident on the parallel flat plates, the reflection rate of the vertical component (P component) differs from the reflection rate of the horizontal component (S component).

Figure 29:
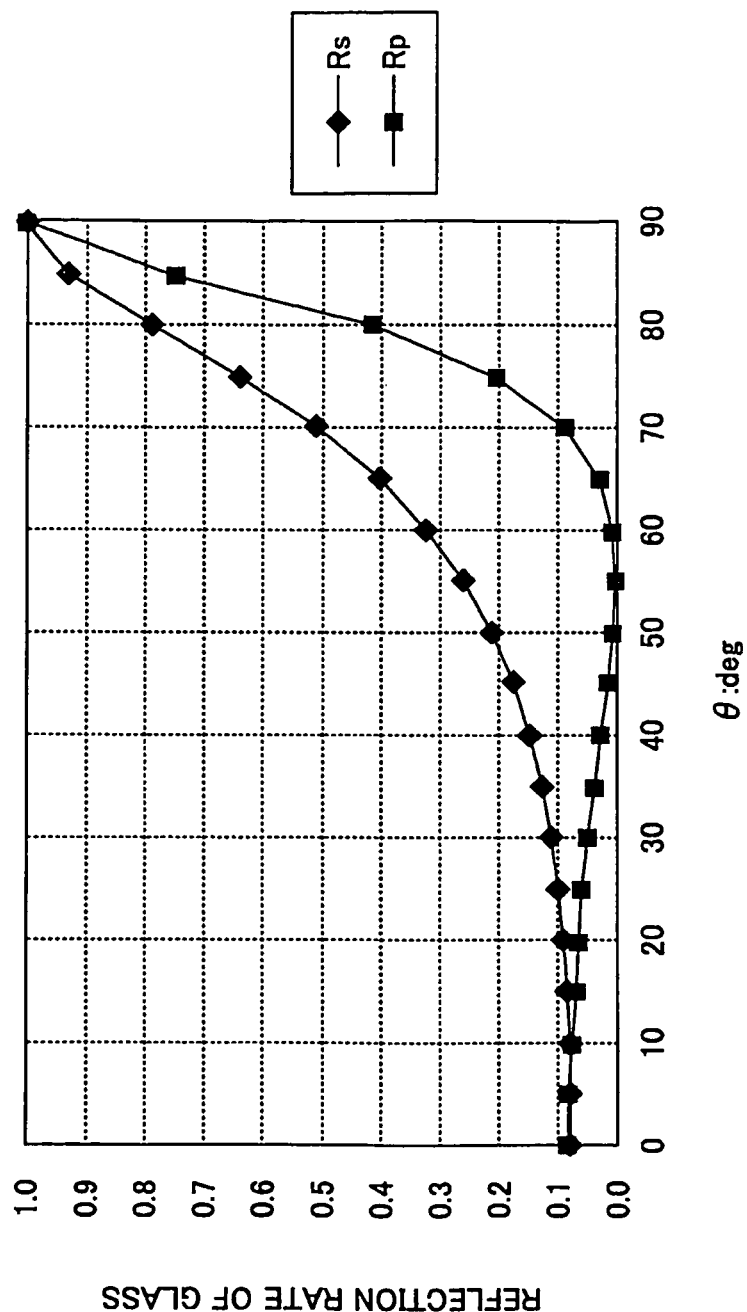
FIG. 29 is a graph illustrating an example of reflection rate of a transparent flat plate.

FIG. 29 illustrates the characteristics of the reflection rate of the light incident on a glass flat plate having a refractive index of 1.5 with an incident angle of θ. Specifically, as illustrated in FIG. 29, the reflection rate of the horizontal component (S component) simply increases. However the reflection rate of the vertical component (P component) decreases first and then increases.

The transparent flat plate detection system 1B uses the change (difference) between the reflection rate of the horizontal component (S component) and the reflection rate of the vertical component (P component). In this case, as illustrated in FIG. 29, when the elevation angle is approximately 70 degrees, the difference between the P component and the S component is large and the reflection rate of the horizontal component (S component) is sufficiently high (20% or more). Therefore, it is preferable to set the elevation angle in a range between, for example, 50 degrees and 70 degrees.

As described above, the camera 12 acquires the vertical/lateral polarization degree image. For example, the vertical/lateral polarization degree image has gradations (gradation values) (e.g., 256 gradations) in the polarization direction from horizontal component (S component) to vertical component (P component). In this case, for example, when light having the S component is incident, dark gradation is displayed. On the other hand, when light having the P component is incident, bright gradation is displayed.

FIGS. 30A and 30B illustrate examples of the images acquired by the camera 12. FIG. 30A illustrates an example of the monochrome luminance image, and FIG. 30B illustrates an example of the vertical/lateral polarization degree image.

As illustrated in FIG. 30B, when a base is selected so that the vertical/lateral polarization degree of the background part where light does not transmit through the transparent flat plate 114B is displayed in dark gradation, the vertical/lateral polarization degree of the region where light transmitted through the transparent flat plate 114B is shifted to the bright gradation side. On the other hand, in the monochrome luminance image of FIG. 30A, only the edge portion of the transparent flat plate 114B is slightly displayed in white. Therefore, in the image processing, it may be difficult to distinguish the transparent flat plate 114B from the placing table 113.

As described above, when the vertical/lateral polarization degree image is used, the part corresponding to the existence region of the transparent flat plate 114B in the acquired image is displayed in the bright gradation or the dark gradation. As a result, the contract between the part and the rest of the part becomes high (clear). Because of this feature, based on the image processing flow described above, it may become possible to detect the existence region of the transparent flat plate 114B and further detect the position, the posture, the size and the like of the transparent flat plate 114B.

As described above, in the transparent flat plate detection system 1B according to this embodiment of the present invention, the change of the polarization condition of the transmission light obliquely incident on the transparent flat plate 114B from the reflection surface 115 is used, and the unnecessary light of the mirror reflection light is blocked. Therefore, the contrast between the part where the transparent flat plate 114B exists and the other part may become high (clear), thereby enabling detecting the transparent flat plate 114B. Further, the vertical/lateral polarization degree image data are acquired. Therefore, without depending on the direction of the polarization filter 112 (base) disposed under the transparent flat plate 114B, it may become possible to detect the polarization change of the transparent flat plate 114B, thereby enabling eliminating the calibration operation. Further, the rotation mechanism may not become necessary (Problem 3 may be resolved). Further, the mirror reflection light from the transparent flat plate 114B is not incident on the image acquisition unit (camera 12) and the light transmitted through the transparent flat plate 114B is used. Therefore, it is not necessary to provide a dedicated lighting apparatus, and even under the fluorescent light 101, it may become possible to detect the transparent flat plate 114B (Problem 1 may be resolved). Further, in a state where the placing table 113 is disposed above the tray and the transparent flat plate 114B is placed on the placing table 113 or in a state where the transparent flat plate 114B is placed directly on the placing table 113, it may become possible to detect the transparent flat plate 114B (Problem 2 may be resolved).

Although the invention has been described with respect to specific embodiments for a complete and clear disclosure, the appended claims are not to be thus limited but are to be construed as embodying all modifications and alternative constructions that may occur to one skilled in the art that fairly fall within the basic teachings herein set forth.

The present application is based on and claims the benefit of priority of Japanese Patent Application Nos. 2010-030238, filed on Feb. 15, 2010 and 2010-030247, filed on Feb. 15, 2010, the entire contents of which are hereby incorporated herein by reference.

The invention claimed is:

1. A transparent body detection system comprising:
an image acquisition unit acquiring a vertical polarization image and a horizontal polarization image by acquiring an image of a first region, the image including a transparent body having characteristics in which a polarization direction of transmission light changes;
a placing table on which the transparent body is to be placed;
a polarization filter disposed opposite to the image acquisition unit across the placing table and at a position including a second region, an image of the second region including at least the transparent body in the first region and being acquired;
an image processing apparatus detecting the transparent body based on distribution of vertical/lateral polarization degree of a vertical/lateral polarization degree image based on the vertical polarization image and the horizontal polarization image; and
a light shielding member shielding indoor light from directly irradiating the transparent body when the transparent body is placed on the placing table under the indoor light.

2. The transparent body detection system according to claim 1, wherein
the image processing apparatus detects a position and a posture of the detected transparent body.

3. The transparent body detection system according to claim 2, further comprising:
a robot hand; and
a robot controller controlling the robot hand, wherein
the robot controller causes the robot hand to move based on the position of the detected transparent body and pick up the transparent body based on the posture of the detected transparent body.

4. The transparent body detection system according to claim 2, wherein
the image processing apparatus determines an existence region of the transparent body based on the position and the posture of the detected transparent body, compares two or more existence regions of the transparent body, and detects a fault in shape of the transparent body.

5. The transparent body detection system according to claim 2, wherein
the image processing apparatus determines an existence region of the transparent body based on the position and the posture of the detected transparent body and detects a fault in appearance of the transparent body based on luminance distribution of a monochrome luminance image based on the vertical polarization image and the horizontal polarization image.

6. The transparent body detection system according to claim 2, wherein
the image processing apparatus determines an existence region of the transparent body based on the position and the posture of the detected transparent body and detects at least one of character information and design pattern information based on luminance distribution of a monochrome luminance image based on the vertical polarization image and the horizontal polarization image, the character information and design pattern information being formed on a surface of the transparent body.

7. The transparent body detection system according to claim 2, wherein
the transparent body is a transparent foreign matter to be mixed in an empty bottle or in a bottle which is filled with transparent fluid, and
the image processing apparatus determines whether the transparent foreign matter is mixed in the empty bottle or in the bottle which is filled with the transparent fluid based on the distribution of the vertical/lateral polarization degree of the vertical/lateral polarization degree image based on the vertical polarization image and the horizontal polarization image.

8. The transparent body detection system according to claim 1, wherein
the placing table has a mesh structure.

9. A transparent flat plate detection system comprising:
an image acquisition unit acquiring a vertical polarization image and a horizontal polarization image by acquiring an image of a region including a transparent flat plate, the image being acquired with a predetermined angle with respect to a normal line of a flat surface part of the transparent flat plate;
a placing table on which the transparent flat plate is to be placed;
a reflection surface disposed on an optical path passing through the transparent flat plate and the image acquisition unit and under the placing table;
a light shielding plate disposed so as to face the image acquisition unit with respect to the normal line of the flat surface part of the transparent flat plate and block light so as to prevent mirror reflection light from the flat surface part of the transparent flat plate from being incident on the image acquisition unit;
an image processing apparatus detecting the transparent flat plate based on distribution of vertical/lateral polarization degree of a vertical/lateral polarization degree image based on the vertical polarization image and the horizontal polarization image; and
a light shielding member shielding indoor light from directly irradiating the transparent flat plate when the transparent flat plate is placed on the placing table under the indoor light.

10. The transparent flat plate detection system according to claim 9, wherein
the image processing apparatus detects a position and a posture of the detected transparent flat plate.

11. The transparent flat plate detection system according to claim 10, further comprising:
a robot hand; and
a robot controller controlling the robot hand, wherein
the robot controller causes the robot hand to move based on the position of the detected transparent flat plate and pick up the transparent flat plate based on the posture of the detected transparent flat plate.

12. The transparent flat plate detection system according to claim 10, wherein
the image processing apparatus determines an existence region of the transparent flat plate based on the position and the posture of the detected transparent flat plate, compares two or more existence regions of the transparent flat plate, and detects a fault in shape of the transparent flat plate.

13. The transparent flat plate detection system according to claim 10, wherein
the image processing apparatus determines an existence region of the transparent flat plate based on the position and the posture of the detected transparent flat plate and detects a fault in appearance of the transparent flat plate based on luminance distribution of a monochrome luminance image based on the vertical polarization image and the horizontal polarization image.

14. The transparent flat plate detection system according to claim 10, wherein
the image processing apparatus determines an existence region of the transparent flat plate based on the position and the posture of the detected transparent flat plate and detects at least one of character information and design pattern information based on luminance distribution of a monochrome luminance image based on the vertical polarization image and the horizontal polarization image, the character information and design pattern information being formed on a surface of the transparent flat plate.

15. The transparent flat plate detection system according to claim 9, wherein
the placing table has a mesh structure.

16. A transparent flat plate detection system comprising:
an image acquisition unit acquiring a vertical polarization image and a horizontal polarization image by acquiring an image of a region including a transparent flat plate, the image being acquired with a predetermined angle with respect to a normal line of a flat surface part of the transparent flat plate;
a reflection surface disposed so as to face the image acquisition unit with respect to the normal line of the flat surface part of the transparent flat plate and having an elevation angle so that mirror reflection light from the flat surface part of the transparent flat plate is incident on the image acquisition unit;

a placing table on which the transparent flat plate is to be placed;

an image processing apparatus detecting the transparent flat plate based on distribution of vertical/lateral polarization degree of a vertical/lateral polarization degree image based on the vertical polarization image and the horizontal polarization image; and a light shielding member shielding indoor light from directly irradiating the transparent flat plate when the transparent flat plate is placed on the placing table under the indoor light.

17. The transparent flat plate detection system according to claim 16, wherein the placing table has a mesh structure.

* * * * *